US010454036B2

(12) United States Patent
Spencer et al.

(10) Patent No.: US 10,454,036 B2
(45) Date of Patent: Oct. 22, 2019

(54) POLYMERIC CHARGE TRANSFER LAYER AND ORGANIC ELECTRONIC DEVICE CONTAINING THE SAME

(71) Applicants: Dow Global Technologies LLC, Midland, MI (US); Rohm and Haas Electronic Materials LLC, Marlborough, MA (US); Rohm and Haas Electronic Materials Korea Ltd., Cheonan (KR)

(72) Inventors: Liam P. Spencer, Manvel, TX (US); Hong-Yeop Na, Seoul (KR); Yoo-Jin Doh, Seoul (KR); Chun Liu, Midland, MI (US); Minrong Zhu, Shanghai (CN); Jichang Feng, Shanghai (CN); Zhengming Tang, Shanghai (CN); Shaoguang Feng, Shanghai (CN); Kenneth L. Kearns, Jr., Midland, MI (US); Timothy De Vries, Midland, MI (US); Sukrit Mukhopadhyay, Midland, MI (US); John W. Kramer, Midland, MI (US); Peter Trefonas, III, Medway, MA (US); David D. Devore, Midland, MI (US); William H. H. Woodward, Harbor Beach, MI (US)

(73) Assignees: Dow Global Technologies LLC, Midland, MI (US); Rohm and Haas Electronic Materials Korea Ltd., Cheonan (KR); Rohm and Haas Electronic Materials LLC, Marlborough, MA (US)

( * ) Notice: Subject to any disclaimer, the term of this patent is extended or adjusted under 35 U.S.C. 154(b) by 197 days.

(21) Appl. No.: 15/504,389

(22) PCT Filed: Jan. 8, 2015

(86) PCT No.: PCT/CN2015/070355
§ 371 (c)(1),
(2) Date: Feb. 16, 2017

(87) PCT Pub. No.: WO2016/026266
PCT Pub. Date: Feb. 25, 2016

(65) Prior Publication Data
US 2018/0226584 A1 Aug. 9, 2018

(30) Foreign Application Priority Data
Aug. 21, 2014 (WO) ................ PCT/CN2014/084915
Aug. 21, 2014 (WO) ................ PCT/CN2014/084918

(51) Int. Cl.
*H01L 51/54* (2006.01)
*H01L 51/00* (2006.01)
(Continued)

(52) U.S. Cl.
CPC ........ *H01L 51/0043* (2013.01); *C07D 209/86* (2013.01); *C08G 61/124* (2013.01); *H01L 51/004* (2013.01); *H01L 51/005* (2013.01); *H01L 51/0034* (2013.01); *C08G 2261/124* (2013.01); *C08G 2261/148* (2013.01); *C08G 2261/1424* (2013.01); *C08G 2261/1434* (2013.01); *C08G 2261/18* (2013.01);
(Continued)

(58) Field of Classification Search
CPC ............ C08G 61/124; C08G 2261/124; C08G 2261/1424; C08G 2261/1434; C08G 2261/148; C08G 2261/18; C08G 2261/228; C08G 2261/312; C08G 2261/3142; C08G 2261/3162; C08G 2261/3141; C08G 2261/512; C08G 2261/95; C07D 209/86; H01L 51/0032; H01L 51/0034; H01L 51/0043; H01L 51/004; H01L 51/005; H01L 51/0003; H01L 51/0059; H01L 51/006; H01L 51/0067; H01L 51/0072; H01L 51/50; H01L 51/5056; H01L 51/5072; H01L 51/506
USPC ....... 428/690, 691, 411.4, 336, 917; 427/58, 427/66; 313/500–512; 257/40, 88–104, 257/E51.001–E51.052; 252/301.16–301.35
See application file for complete search history.

(56) References Cited

U.S. PATENT DOCUMENTS

| 4,639,496 A | 1/1987 | Weddigen et al. |
| 7,534,853 B2 | 5/2009 | Stossel et al. |

(Continued)

FOREIGN PATENT DOCUMENTS

| CN | 103044661 A | 4/2013 |
| CN | 103288712 A | 9/2013 |
| JP | 2012177029 A | 9/2012 |

OTHER PUBLICATIONS

Gao, et al, "Comparative studies on the inorganic and organic p-type dopants in organic light-emitting diodes with enhanced hole injection", Applied Physics Letters, Apr. 2013, pp. 153301-1, vol. 102, No. 15.
(Continued)

*Primary Examiner* — Andrew K Bohaty
(74) *Attorney, Agent, or Firm* — S. Matthew Cairns

(57) ABSTRACT

The present invention relates to a polymeric charge transfer layer comprising a polymer and a p-dopant. The polymer comprises as polymerized units, Monomer A, Monomer B, and Monomer C crosslinking agent. The present invention further relates to an organic electronic device, especially an organic light emitting device containing the polymeric charge transfer layer.

12 Claims, 1 Drawing Sheet

(51) Int. Cl.
   *C07D 209/86* (2006.01)
   *C08G 61/12* (2006.01)
   *H01L 51/50* (2006.01)

(52) U.S. Cl.
   CPC . *C08G 2261/228* (2013.01); *C08G 2261/312* (2013.01); *C08G 2261/3142* (2013.01); *C08G 2261/3162* (2013.01); *C08G 2261/3241* (2013.01); *C08G 2261/512* (2013.01); *C08G 2261/95* (2013.01); *H01L 51/0003* (2013.01); *H01L 51/506* (2013.01); *H01L 51/5056* (2013.01); *H01L 51/5072* (2013.01)

(56) References Cited

U.S. PATENT DOCUMENTS

| | | |
|---|---|---|
| 8,429,796 B2 | 4/2013 | Nagami et al. |
| 9,293,709 B2 | 3/2016 | Pillow |
| 2003/0062509 A1 | 4/2003 | Heeney et al. |
| 2009/0315453 A1 | 12/2009 | Kobayashi et al. |
| 2011/0108814 A1 | 5/2011 | Iida et al. |
| 2011/0198573 A1 | 8/2011 | Iida et al. |
| 2012/0001127 A1* | 1/2012 | Brown .................. C07D 403/00 252/500 |
| 2013/0015430 A1* | 1/2013 | Kwong ............... H01L 51/0032 257/40 |
| 2013/0085258 A1 | 4/2013 | Gaynor et al. |
| 2014/0235800 A1* | 8/2014 | Humphries ............ C08G 61/12 525/539 |

OTHER PUBLICATIONS

Search report for corresponding European Application No. 15 83 3181 dated Mar. 14, 2018.
Chinese Search Report for application No. 201580043855.5; dated Jan. 8, 2015.
European Examination Report for application No. 15833181.9; dated Jan. 8, 2015.
Taiwanese Examination Report for application No. 104142369; dated Dec. 16, 2015.

* cited by examiner

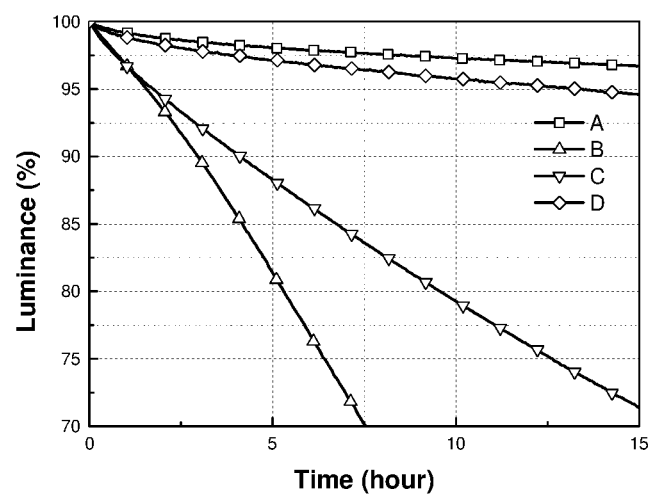

POLYMERIC CHARGE TRANSFER LAYER AND ORGANIC ELECTRONIC DEVICE CONTAINING THE SAME

FIELD OF THE INVENTION

The present invention relates to a polymeric charge transfer layer comprising a polymer and a p-dopant. The polymer comprises as polymerized units, Monomer A, Monomer B, and Monomer C crosslinking agent. The present invention further relates to an organic electronic device, especially, a light emitting device containing the polymeric charge transfer layer.

INTRODUCTION

Organic electronic devices are devices that carry out electrical operations using at least one organic material. They are endowed with advantages such as flexibility, low power consumption, and relatively low cost over conventional inorganic electronic devices. Organic electronic devices usually include organic light emitting devices, organic solar cells, organic memory devices, organic sensors, organic thin film transistors, and power generation and storage devices such as organic batteries, fuel cells, and organic supercapacitors. Such organic electronic devices are prepared from hole injection or transportation materials, electron injection or transportation materials, or light emitting materials.

A typical organic light emitting device is an organic light emitting diode (OLED) having a multi-layer structure, and typically includes an anode, and a metal cathode. Sandwiched between the anode and the metal cathode are several organic layers such as a hole injection layer (HIL), a hole transfer layer (HTL), an emitting layer (EL), an electron transfer layer (ETL) and an electron injection layer (EIL). New material discovery for ETL and HTL in OLEDs have been targeted to improve device performance and lifetimes. In the case of HTL layer, as a typical polymeric charge transfer layer, the process by which the layer is deposited is critical for its end-use application. Methods for depositing HTL layer, in small display applications, involve evaporation of a small organic compound with a fine metal mask to direct the deposition. In the case of large displays, this approach is not practical from a material usage and high throughput perspective. With these findings in mind, new processes are needed to deposit HTLs that satisfy these challenges, and which can be directly applied to large display applications.

One approach that appears promising is a solution process which involves the deposition of a small molecule HTL material attached with crosslinking or polymerization moiety. Solution process based methods include spin-coating, inkjet printing, and screen printing which are well-known in the art. There have been extensive efforts in this area, along these lines; however, these approaches have their own shortcomings. In particular, the mobility of the charges in the HTL becomes reduced, as a result of crosslinking or polymerization chemistry. This reduced hole mobility leads to poor device lifetime.

Therefore, it is still desired to provide new polymeric charge transfer layer compositions for organic electronic devices, specifically for organic light emitting devices, organic solar cells, or organic memory devices with improved device lifetime.

SUMMARY OF THE INVENTION

The present invention provides a polymeric charge transfer layer, and an organic electronic device, especially a light emitting device comprising the polymeric charge transfer layer. The polymeric charge transfer layer is formed from a composition comprising, from 1 wt % to 20 wt % based on total weight of the composition, a p-dopant component; and a polymer comprising, as polymerized units, Monomer A, and Monomer C crosslinking agent.

Monomer A has Structure A:

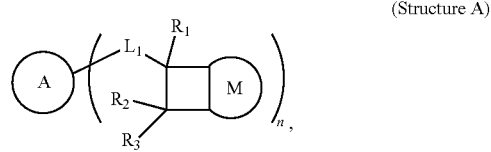

(Structure A)

wherein A and M are each substituted or unsubstituted aromatic moiety or a substituted or unsubstituted heteroaromatic moiety; and wherein n is from 2 to 10; and wherein $R_1$ through $R_3$ are each independently selected from the following: hydrogen; deuterium; a hydrocarbyl, further a $C_1$-$C_{100}$ hydrocarbyl, further a $C_3$-$C_{100}$ hydrocarbyl, further a $C_{10}$-$C_{100}$ hydrocarbyl, further a $C_{20}$-$C_{100}$ hydrocarbyl, further a $C_{30}$-$C_{100}$ hydrocarbyl; a substituted hydrocarbyl, further a $C_1$-$C_{100}$ substituted hydrocarbyl, further a $C_3$-$C_{100}$ substituted hydrocarbyl, further a $C_{10}$-$C_{100}$ substituted hydrocarbyl, further a $C_{20}$-$C_{100}$ substituted hydrocarbyl, further a $C_{30}$-$C_{100}$ substituted hydrocarbyl; a heterohydrocarbyl, further a $C_1$-$C_{100}$ heterohydrocarbyl, further a $C_3$-$C_{100}$ heterohydrocarbyl, further a $C_{10}$-$C_{100}$ heterohydrocarbyl, further a $C_{20}$-$C_{100}$ heterohydrocarbyl, further a $C_{30}$-$C_{100}$ heterohydrocarbyl; a substituted heterohydrocarbyl, further a $C_1$-$C_{100}$ substituted heterohydrocarbyl, further a $C_3$-$C_{100}$ substituted heterohydrocarbyl, further a $C_{10}$-$C_{100}$ substituted heterohydrocarbyl, further a $C_{20}$-$C_{100}$ substituted heterohydrocarbyl, further a $C_{30}$-$C_{100}$ substituted heterohydrocarbyl; a halogen; a cyano; an aryl, further a $C_5$-$C_{100}$ aryl, further a $C_6$-$C_{100}$ aryl, further a $C_{10}$-$C_{100}$ aryl, further a $C_{20}$-$C_{100}$ aryl, further a $C_{30}$-$C_{100}$ aryl; a substituted aryl, further a $C_5$-$C_{100}$ substituted aryl, further a $C_6$-$C_{100}$ substituted aryl, further a $C_{10}$-$C_{100}$ substituted aryl, further a $C_{20}$-$C_{100}$ substituted aryl, further a $C_{30}$-$C_{100}$ substituted aryl; a heteroaryl, further a $C_5$-$C_{100}$ heteroaryl, further a $C_6$-$C_{10}$ heteroaryl, further a $C_{10}$-$C_{100}$ heteroaryl, further a $C_{20}$-$C_{100}$ heteroaryl, further a $C_{30}$-$C_{100}$ heteroaryl; a substituted heteroaryl, further a $C_5$-$C_{100}$ substituted heteroaryl, further a $C_6$-$C_{100}$ substituted heteroaryl, further a $C_{10}$-$C_{100}$ substituted heteroaryl, further a $C_{20}$-$C_{100}$ substituted heteroaryl, further a $C_{30}$-$C_{100}$ substituted heteroaryl; and wherein $L_1$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, and a $C_1$-$C_{100}$ substituted heterohydrocarbyl; and wherein two or more of $R_1$ through $R_3$ may optionally form one or more ring structures.

Monomer C crosslinking agent has Structure C:

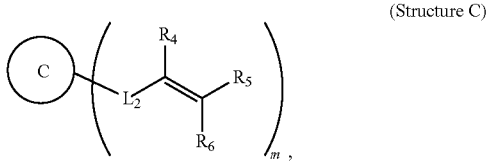
(Structure C)

wherein C is an aromatic moiety, a heteroaromatic moiety, a $C_1$-$C_{50}$ hydrocarbyl, a $C_1$-$C_{50}$ substituted hydrocarbyl, a $C_1$-$C_{50}$ heterohydrocarbyl, or a $C_1$-$C_{50}$ substituted heterohydrocarbyl; and wherein $R_4$ through $R_6$ are each independently selected from the following: hydrogen, deuterium, a $C_1$-$C_{50}$ hydrocarbyl, a $C_1$-$C_{50}$ substituted hydrocarbyl, a $C_1$-$C_{50}$ heterohydrocarbyl, a $C_1$-$C_{50}$ substituted heterohydrocarbyl, halogen, cyano, a $C_5$-$C_{50}$ aryl, a $C_5$-$C_{50}$ substituted aryl, a $C_5$-$C_{50}$ heteroaryl, a $C_5$-$C_{50}$ substituted heteroaryl; and wherein $L_2$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, or a $C_1$-$C_{100}$ substituted heterohydrocarbyl; and wherein m is from 2 to 25; and wherein each chemical group of $L_2$ is independently bonded to C; and wherein two or more of $R_4$ through $R_6$ may optionally form one or more ring structures.

The p-dopant is selected from tropylium salts, imidazolium salts, and trityl salts.

BRIEF DESCRIPTION OF THE DRAWING

FIG. 1 depicts the luminescence decay curves of OLED Devices A to D; OLED Devices A and D showed slower decay rates compared to those of OLED Devices B and C, and none of the OLED Devices A to D showed overshooting phenomena.

DETAILED DESCRIPTION OF THE INVENTION

The polymeric charge transfer layer composition of the present invention comprises from 1 wt % to 20 wt %, preferably from 3 wt % to 15 wt %, and more preferably from 5 wt % to 12 wt %, based on total weight of the composition, a p-dopant component, and a polymer comprising, as polymerized units, Monomer A, optional Monomer B, and Monomer C crosslinking agents.

The Polymer

The polymer comprises Monomer A having a Structure A:

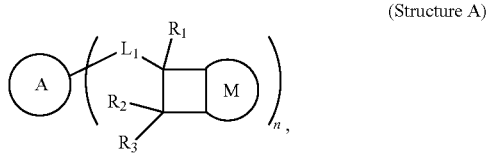
(Structure A)

wherein A and M are each substituted or unsubstituted aromatic moiety or a substituted or unsubstituted heteroaromatic moiety; and wherein n is from 2 to 10; and wherein $R_1$ through $R_3$ are each independently selected from the following: hydrogen; deuterium; a hydrocarbyl, further a $C_1$-$C_{100}$ hydrocarbyl, further a $C_3$-$C_{100}$ hydrocarbyl, further a $C_{10}$-$C_{100}$ hydrocarbyl, further a $C_{20}$-$C_{100}$ hydrocarbyl, further a $C_{30}$-$C_{100}$ hydrocarbyl; a substituted hydrocarbyl, further a $C_1$-$C_{100}$ substituted hydrocarbyl, further a $C_3$-$C_{100}$ substituted hydrocarbyl, further a $C_{10}$-$C_{100}$ substituted hydrocarbyl, further a $C_{20}$-$C_{100}$ substituted hydrocarbyl, further a $C_{30}$-$C_{100}$ substituted hydrocarbyl; a heterohydrocarbyl, further a $C_1$-$C_{100}$ heterohydrocarbyl, further a $C_3$-$C_{100}$ heterohydrocarbyl, further a $C_{10}$-$C_{100}$ heterohydrocarbyl, further a $C_{20}$-$C_{100}$ heterohydrocarbyl, further a $C_{30}$-$C_{100}$ heterohydrocarbyl; a substituted heterohydrocarbyl, further a $C_1$-$C_{100}$ substituted heterohydrocarbyl, further a $C_3$-$C_{100}$ substituted heterohydrocarbyl, further a $C_{10}$-$C_{100}$ substituted heterohydrocarbyl, further a $C_{20}$-$C_{100}$ substituted heterohydrocarbyl, further a $C_{30}$-$C_{100}$ substituted heterohydrocarbyl; a halogen; a cyano; an aryl, further a $C_5$-$C_{100}$ aryl, further a $C_6$-$C_{100}$ aryl, further a $C_{10}$-$C_{100}$ aryl, further a $C_{20}$-$C_{100}$ aryl, further a $C_{30}$-$C_{100}$ aryl; a substituted aryl, further a $C_5$-$C_{100}$ substituted aryl, further a $C_6$-$C_{100}$ substituted aryl, further a $C_{10}$-$C_{100}$ substituted aryl, further a $C_{20}$-$C_{100}$ substituted aryl, further a $C_{30}$-$C_{100}$ substituted aryl; a heteroaryl, further a $C_5$-$C_{100}$ heteroaryl, further a $C_6$-$C_{10}$ heteroaryl, further a $C_{10}$-$C_{100}$ heteroaryl, further a $C_{20}$-$C_{100}$ heteroaryl, further a $C_{30}$-$C_{100}$ heteroaryl; a substituted heteroaryl, further a $C_5$-$C_{100}$ substituted heteroaryl, further a $C_6$-$C_{100}$ substituted heteroaryl, further a $C_{10}$-$C_{100}$ substituted heteroaryl, further a $C_{20}$-$C_{100}$ substituted heteroaryl, further a $C_{30}$-$C_{100}$ substituted heteroaryl; and wherein $L_1$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, and a $C_1$-$C_{100}$ substituted heterohydrocarbyl; and wherein two or more of $R_1$ through $R_3$ may optionally form one or more ring structures.

In one embodiment, Monomer A is selected from the following A1 through A12:

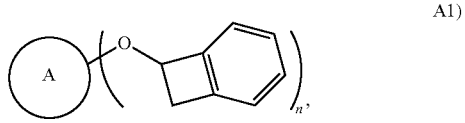
A1)

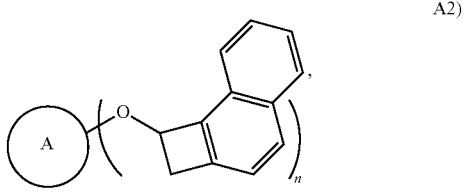
A2)

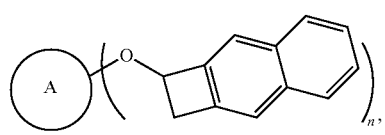 A3)
 A4)
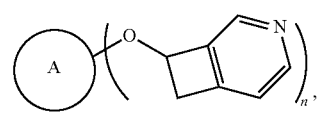 A5)
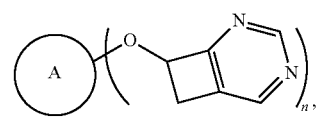 A6)
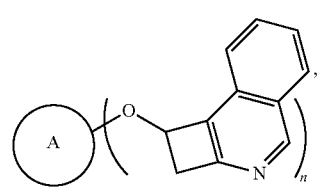 A7)
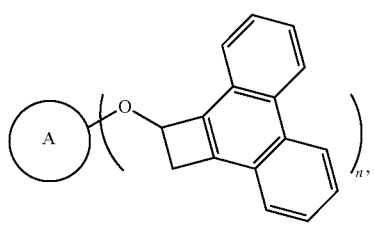 A8)
 A9)
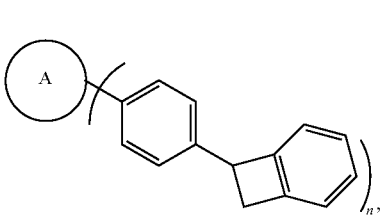 A10)
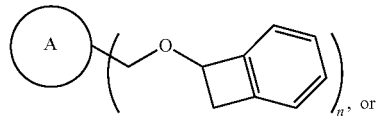 A11)
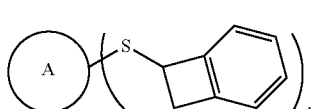 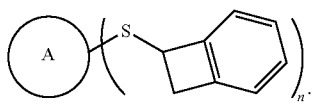 A12)
In one embodiment, Structure A is selected from the following A13 through A28:

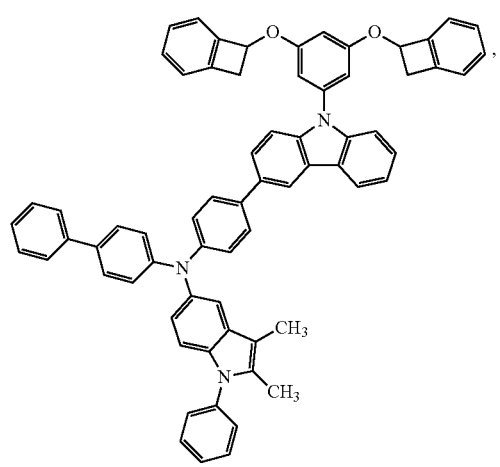 A13)
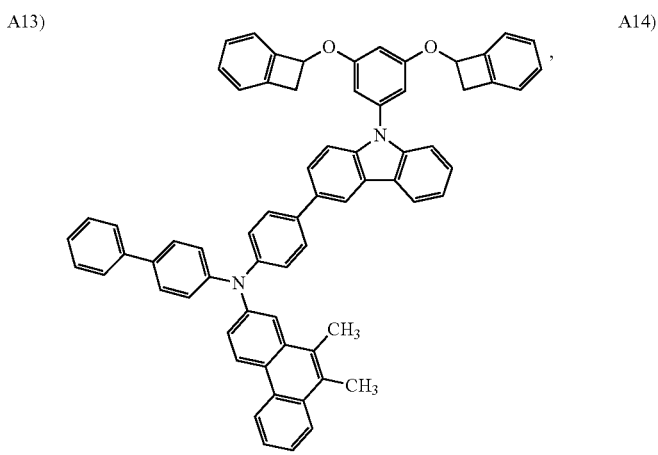 A14)
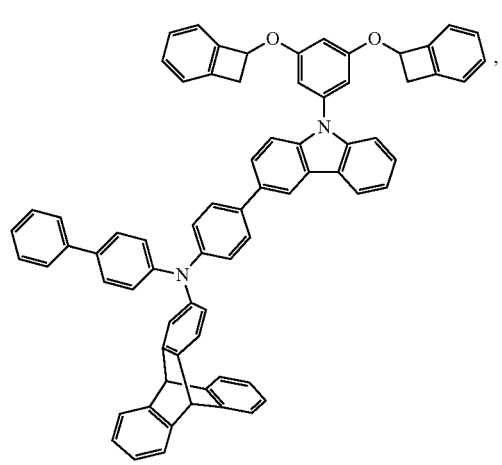 A15)
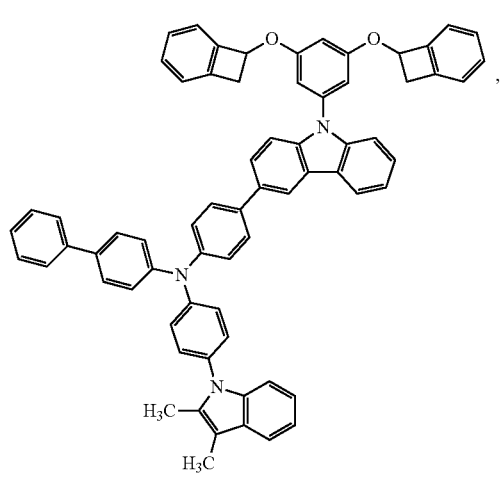 A16)
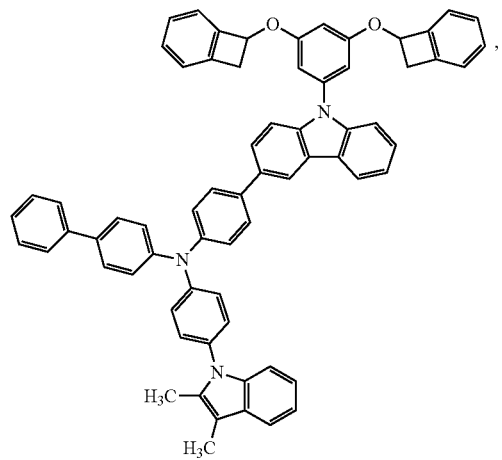 A17)
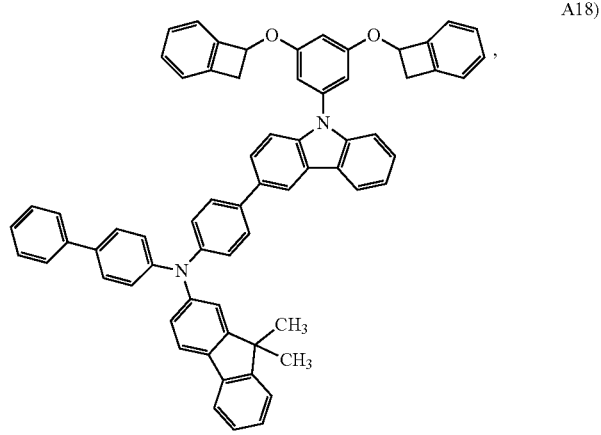 A18)

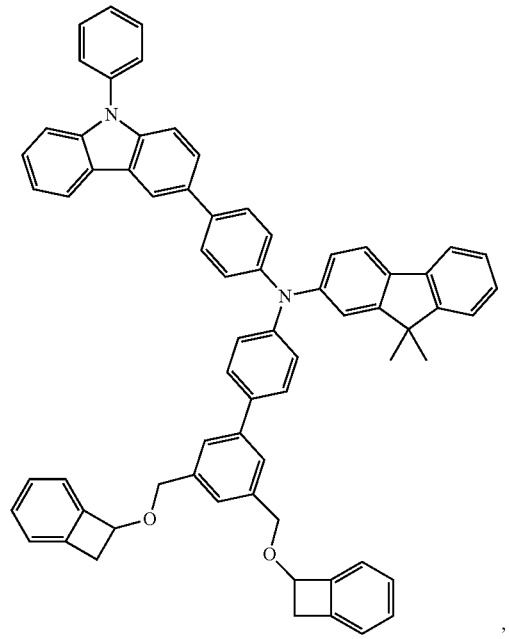
A19)
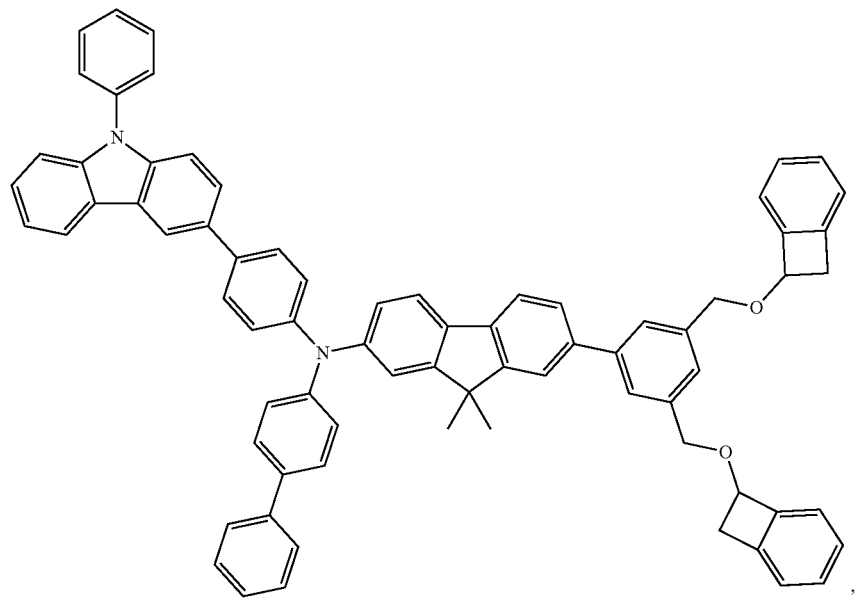
A20)

-continued
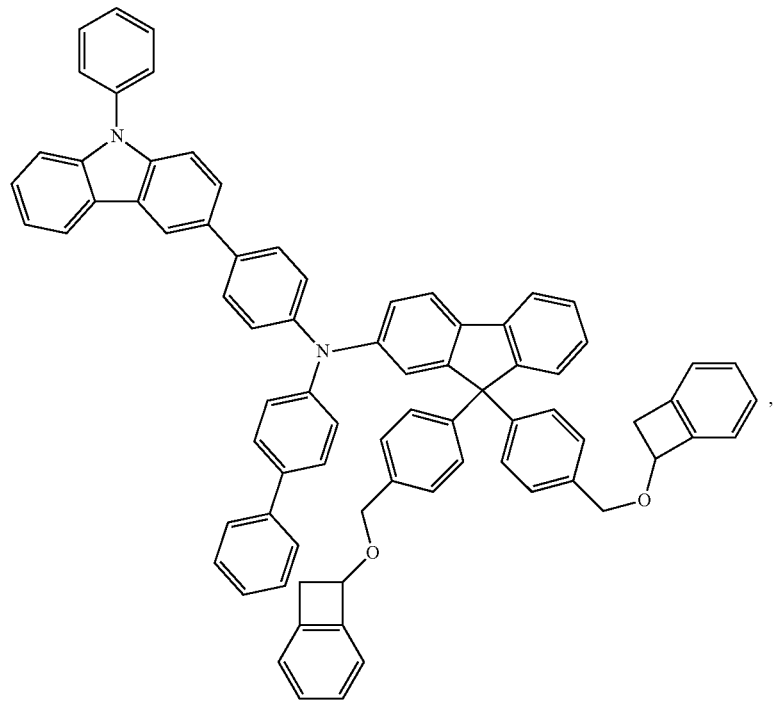
A21)
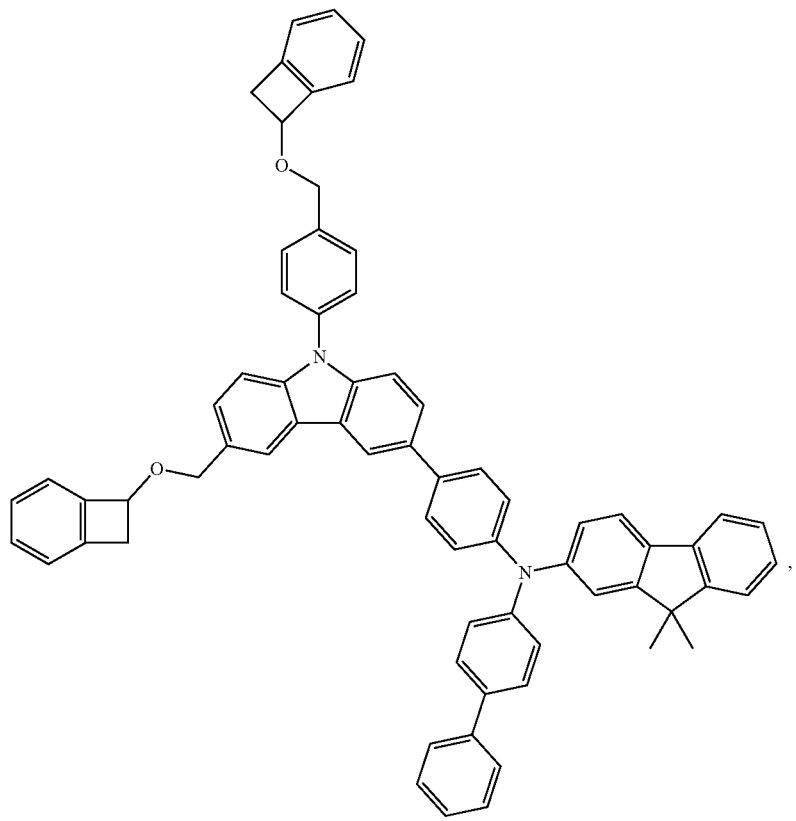
A22)

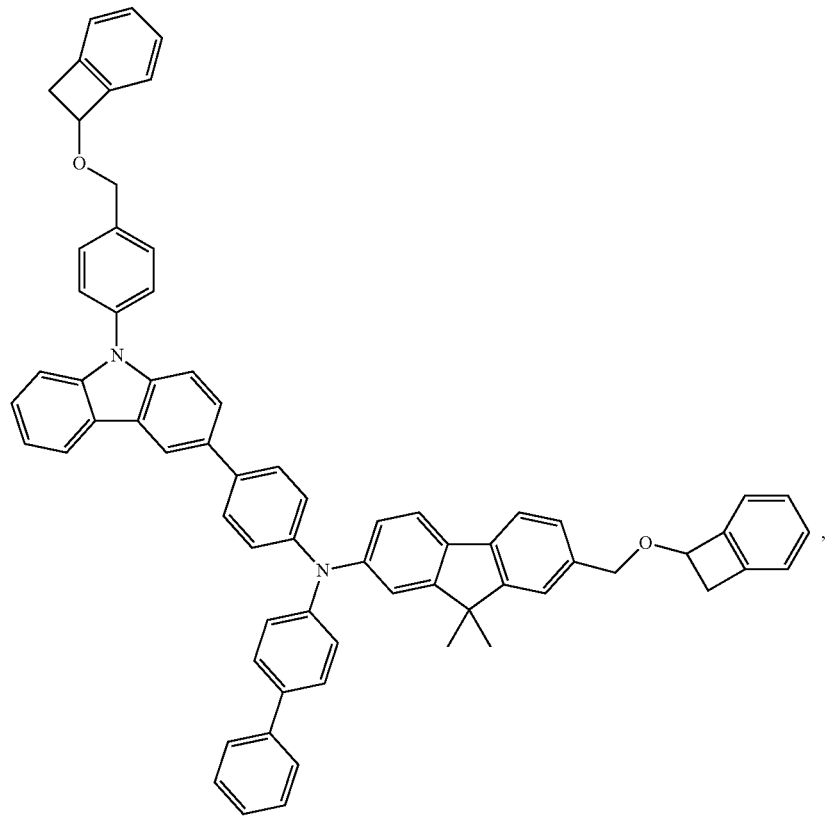
A23)
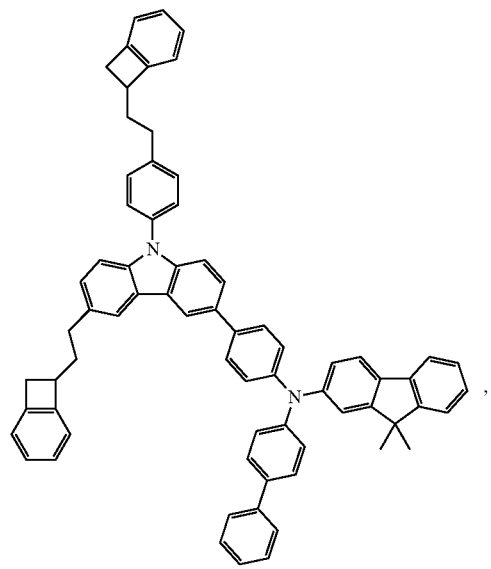
A24)
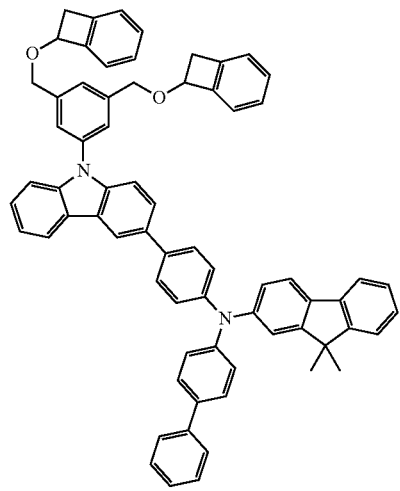
A25)

-continued
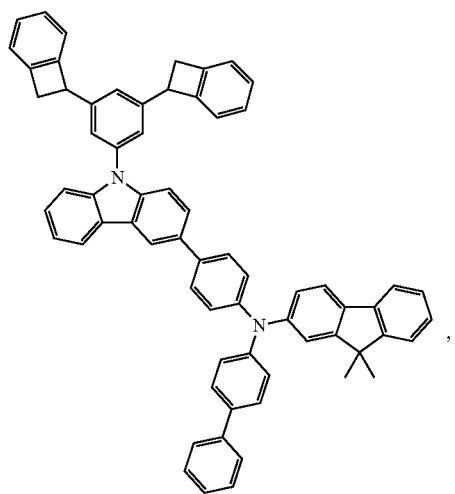
A26)
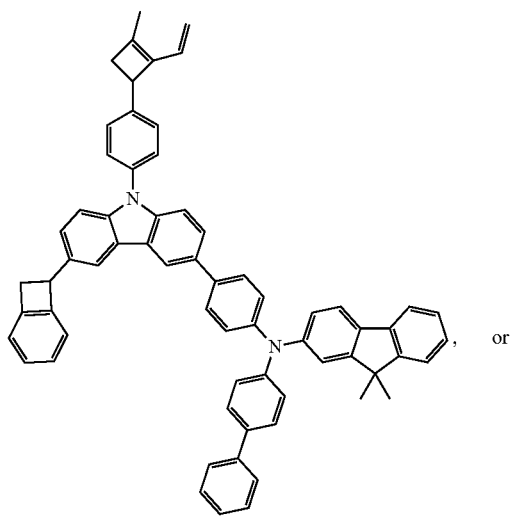
A27) , or
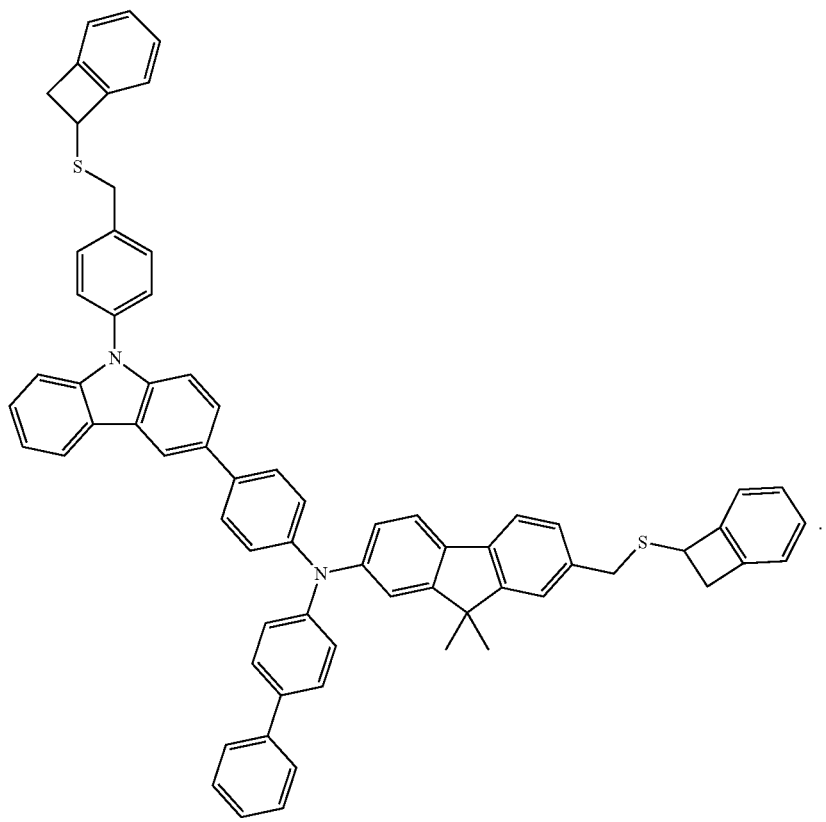
A28) .

Optionally, the polymer further comprises Monomer B comprising at least two dienophile moieties and has a Structure B:

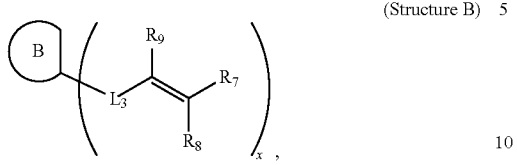
(Structure B)

wherein B is a substituted or unsubstituted aromatic moiety or a substituted or unsubstituted heteroaromatic moiety; and wherein $L_3$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, and a $C_1$-$C_{100}$ substituted heterohydrocarbyl; and wherein x is from 2 to 10; and wherein $R_7$ through $R_9$ are each independently selected from the following: hydrogen, deuterium, a $C_1$-$C_{50}$ hydrocarbyl, a $C_1$-$C_{50}$ substituted hydrocarbyl, a $C_1$-$C_{50}$ heterohydrocarbyl, a $C_1$-$C_{50}$ substituted heterohydrocarbyl, halogen, cyano, a $C_5$-$C_{50}$ aryl, a $C_5$-$C_{50}$ substituted aryl, a $C_5$-$C_{50}$ heteroaryl, and a $C_5$-$C_{50}$ substituted heteroaryl; and wherein two or more of $R_7$ through $R_9$ may optionally form one or more ring structures.

In one embodiment, Monomer B is selected from the following B1 through B6:

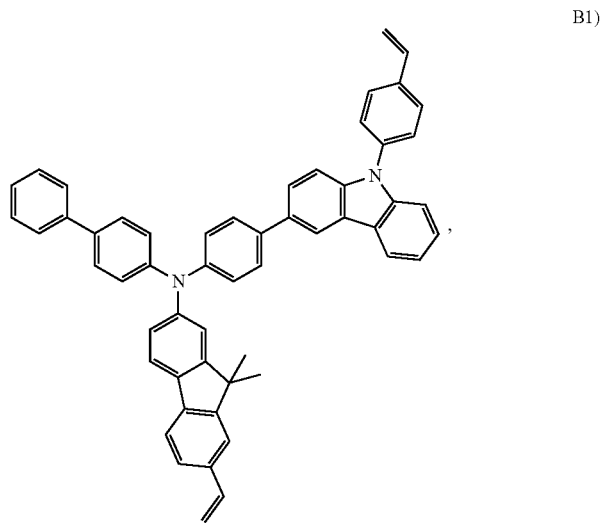
B1)

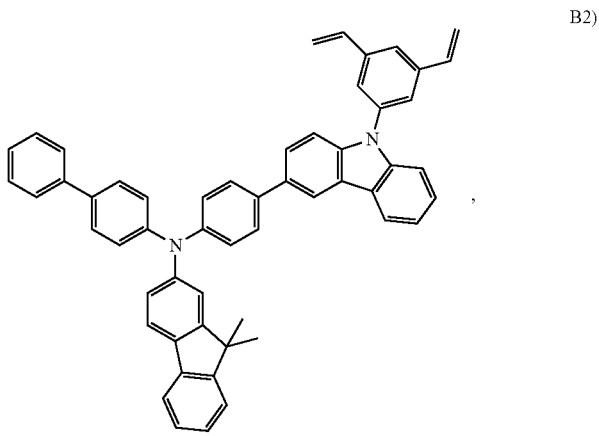
B2)

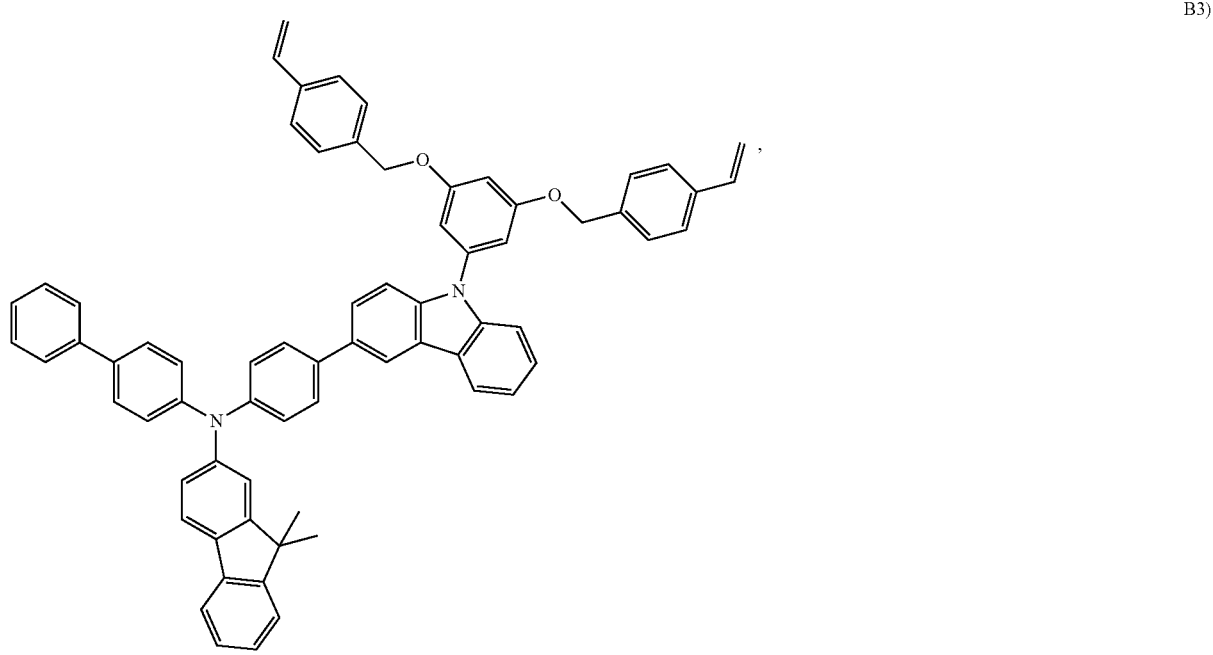
B3)

-continued
B4)
B5)
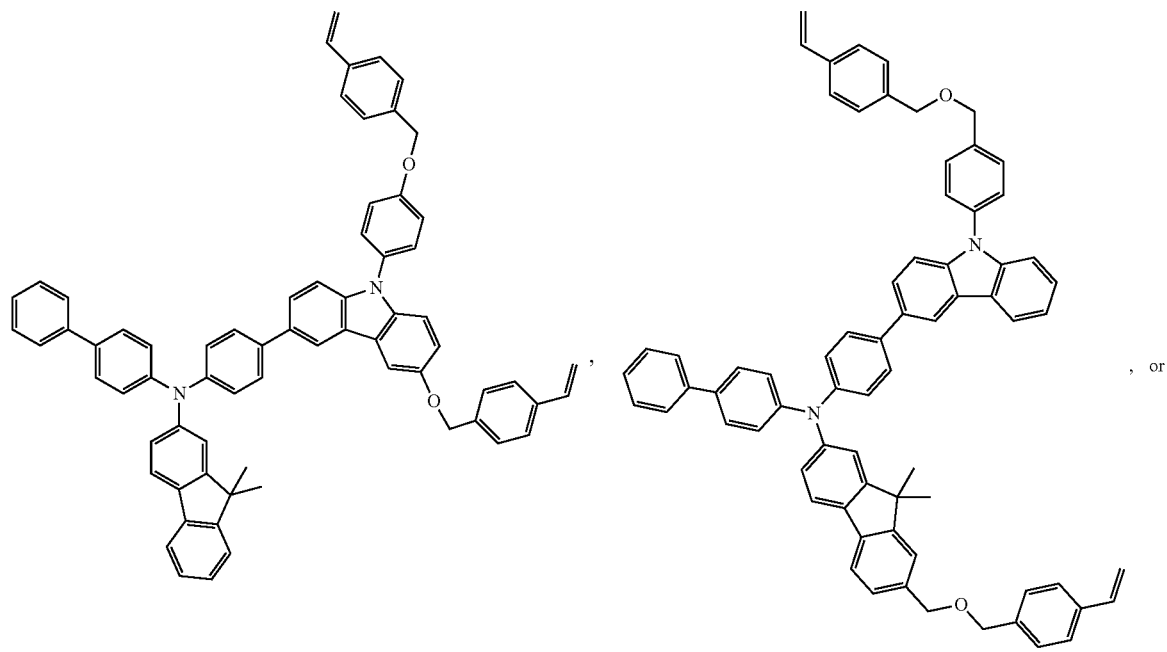
, or
B6)
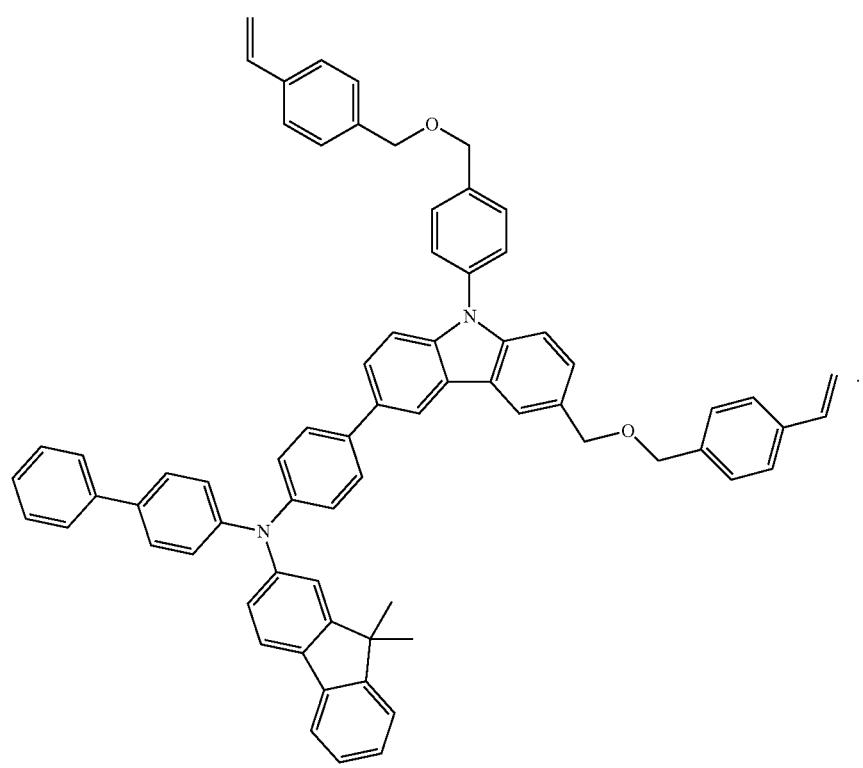
.

The polymer further comprises Monomer C crosslinking agent having Structure C:

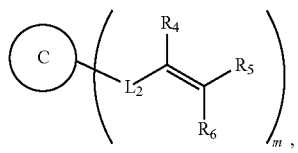
(Structure C)

wherein C is an aromatic moiety, a heteroaromatic moiety, a $C_1$-$C_{50}$ hydrocarbyl, a $C_1$-$C_{50}$ substituted hydrocarbyl, a $C_1$-$C_{50}$ heterohydrocarbyl, or a $C_1$-$C_{50}$ substituted heterohydrocarbyl; and wherein $R_4$ through $R_6$ are each independently selected from the following: hydrogen, deuterium, a $C_1$-$C_{50}$ hydrocarbyl, a $C_1$-$C_{50}$ substituted hydrocarbyl, a $C_1$-$C_{50}$ heterohydrocarbyl, a $C_1$-$C_{50}$ substituted heterohydrocarbyl, halogen, cyano, a $C_5$-$C_{50}$ aryl, a $C_5$-$C_{50}$ substituted aryl, a $C_5$-$C_{50}$ heteroaryl, a $C_5$-$C_{50}$ substituted heteroaryl; and wherein $L_2$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, or a $C_1$-$C_{100}$ substituted heterohydrocarbyl; and wherein m is from 2 to 25; and wherein each chemical group of $L_2$ is independently bonded to C; and wherein two or more of $R_4$ through $R_6$ may optionally form one or more ring structures.

In one embodiment, the crosslinking agent is selected from the following C1-C11:

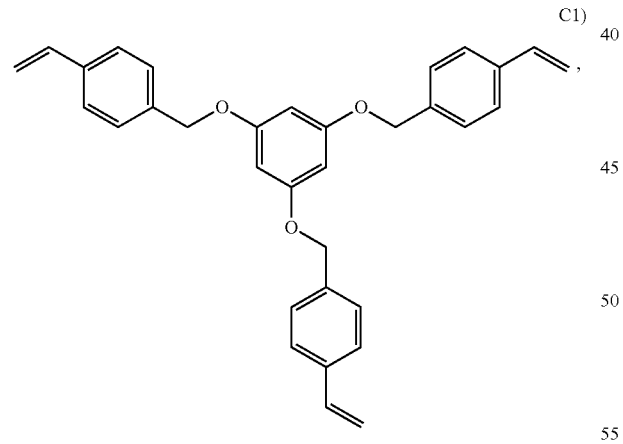
C1)

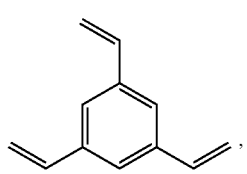
C2)

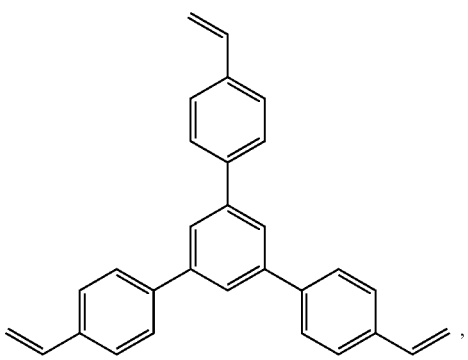
C3)

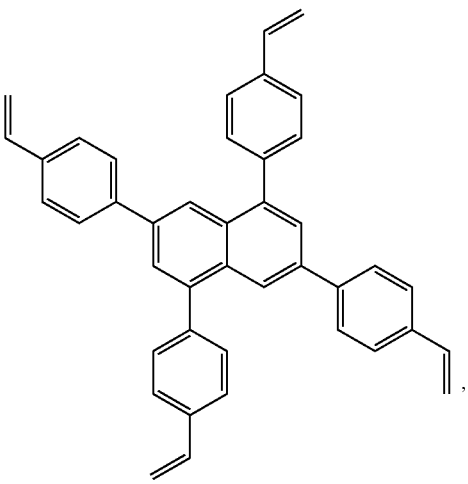
C4)

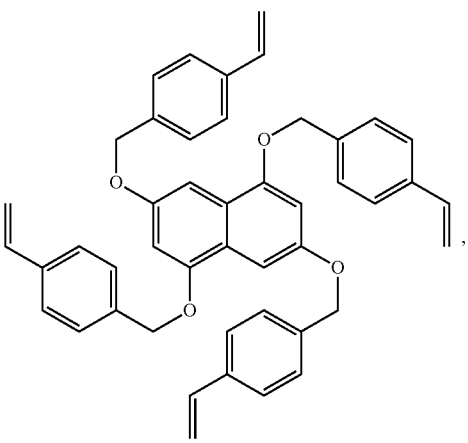
C5)

C6)
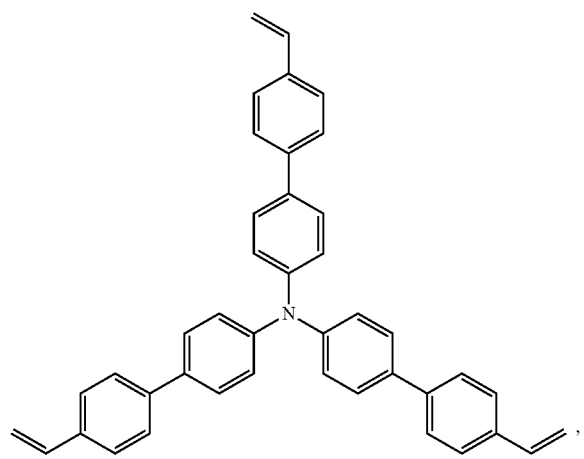

C7)
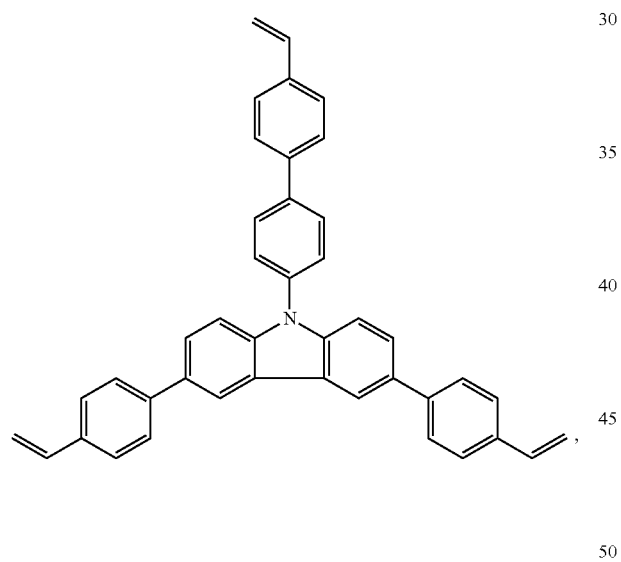

C8)
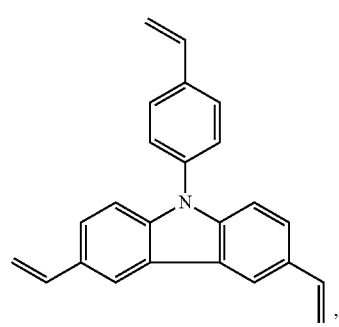

C9)
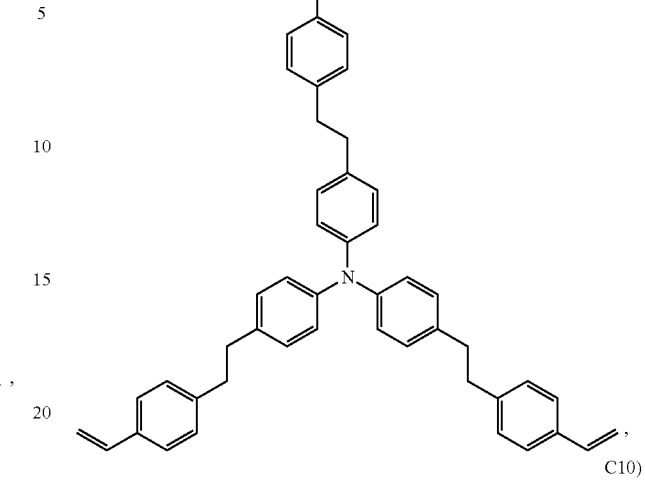

C10), or

C11)

In one embodiment, Monomer C crosslinking agent is present in an amount from 0.1 to 50 mole %, preferably from 0.5 to 15 mole %, and more preferably from 5 to 12 mole % based on the sum moles of Monomer A (Structure A).

In one embodiment, the molar ratio of Monomer A to Monomer B is from 0.8 to 1.2, and preferably from 0.9 to 1.1.

In one embodiment, the molecule weight of either of Monomer A, Monomer B, and Monomer C is from 500 g/mole to 28000 g/mole, preferably from 700 g/mole to 14000 g/mole, and more preferably from 1000 g/mole to 4000 g/mole.

In one embodiment, the purity of either of Monomer A, Monomer B and Monomer C is equal to or above 99%, preferably is equal to or above 99.4%, and more preferably is equal to or above 99.5%. The said purify is achieved through well-known methods in the art to remove the impurities, and includes fractionation, sublimation, chromatography, crystallization and precipitation methods.

In one embodiment, either of Monomer A, Monomer B and Monomer C is further purified through ion exchange beads to remove cationic impurities and anionic impurities, such as metal ion, sulfate ion, formate ion, oxalate ion and acetate ion.

The P-DOPANT

In one embodiment, the p-dopant is selected from tropylium salts, imidazolium salts, and trityl salts.

In yet another embodiment, the p-dopant has a structure selected from one of the following:

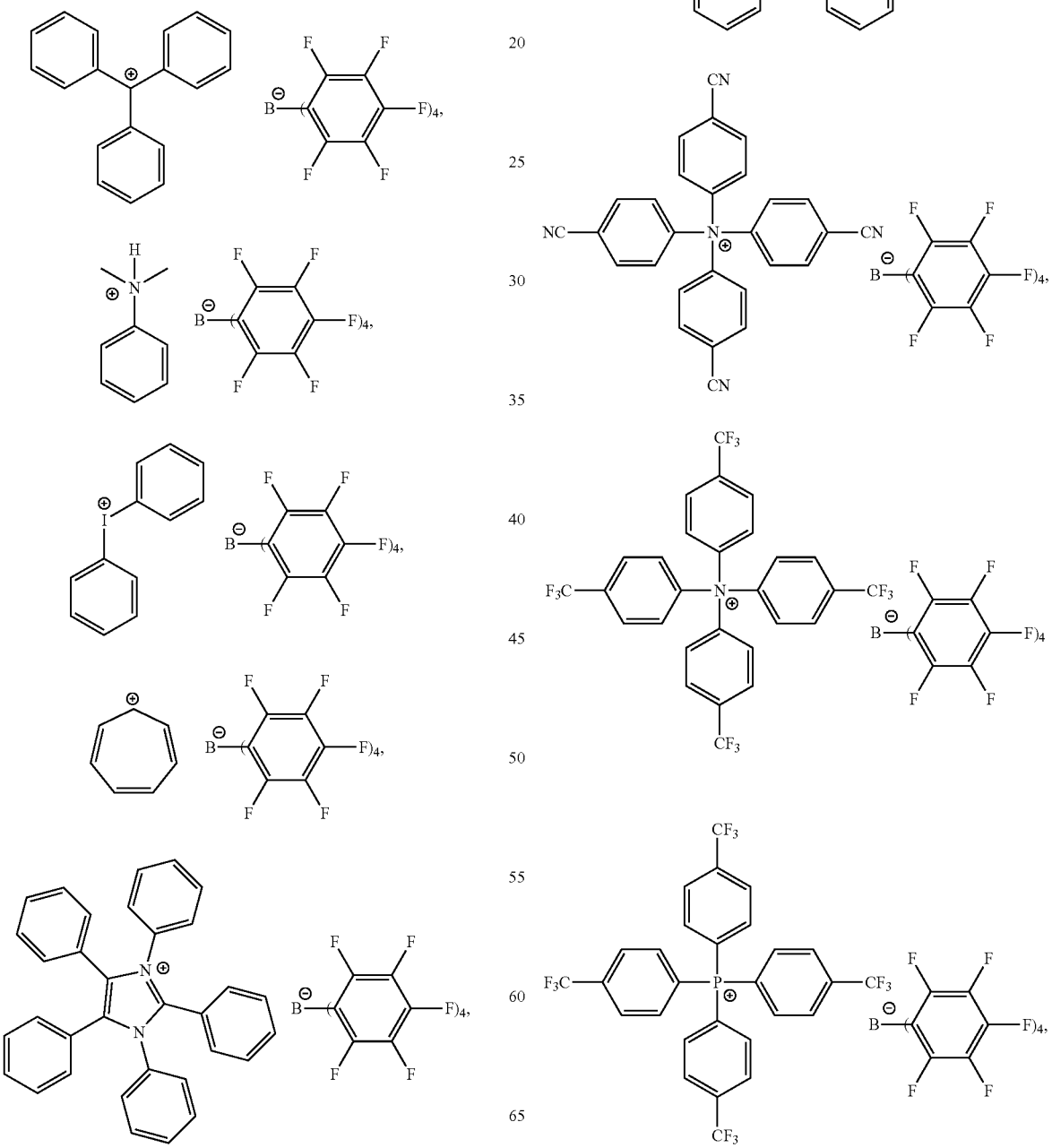

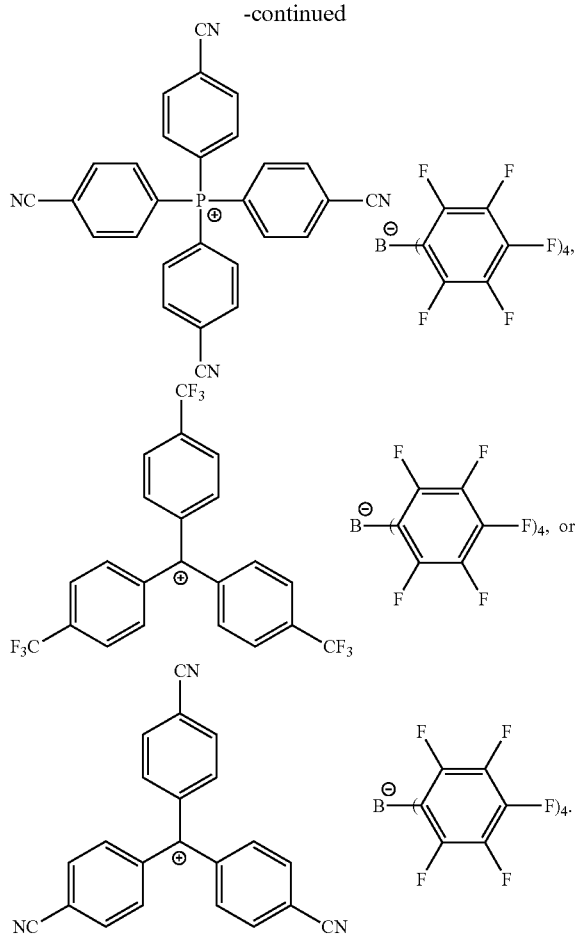

Preferably, the p-dopant has the structure:

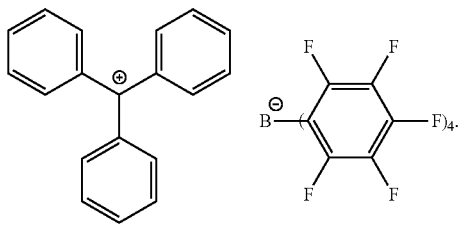

Organic Electronic Device

The present invention provides a method of making an organic electronic device. The method comprises providing a polymeric charge transfer layer solution, and dissolving or dispersing the polymeric charge transfer layer solution in any of the organic solvents known or proposed to be used in the fabrication of an organic electronic device by solution process. Such organic solvents include including tetrahydrofuran (THF), cyclohexanone, chloroform, 1,4-dioxane, acetonitrile, ethyl acetate, tetralin, chlorobenzene, toluene, xylene, anisole, mesitylene, tetralone, and any combination thereof. The polymeric charge transfer layer solution was filtered through a membrane or a filter to remove particles larger than 50 nm.

The polymeric charge transfer layer solution is then deposited over a first electrode, which may be an anode or cathode. The deposition may be performed by any of various types of solution processing techniques known or proposed to be used for fabricating light emitting devices. For example, the polymeric charge transfer layer solution can be deposited using a printing process, such as inkjet printing, nozzle printing, offset printing, transfer printing, or screen printing; or for example, using a coating process, such as spray coating, spin coating, or dip coating. After deposition of the solution, the solvent is removed, which may be performed by using conventional method such as vacuum drying or heating.

The polymeric charge transfer layer solution is further cross-linked to form the layer. Cross-linking may be performed by exposing the layer solution to heat and/or actinic radiation, including UV light, gamma rays, or x-rays. Cross-linking may be carried out in the presence of an initiator that decomposed under heat or irradiation to produce free radicals or ions that initiate the cross-linking reaction. The cross-linking may be performed in-situ during the fabrication of a device. After cross-linking, the polymeric charge transfer layer made thereof is preferably free of residual moieties which are reactive or decomposable with exposure to light, positive charges, negative charges or excitons.

The process of solution deposition and cross-linking can be repeated to create multiple layers.

The organic light emitting device of the present invention comprises a first conductive layer, an electron transport layer (ETL) and a hole transport layer (HTL) and a second conductive layer. The hole transport layer, as the typical polymeric charge transfer layer, is prepared according to the above process. The first conductive layer is used as an anode and in general is a transparent conducting oxide, for example, fluorine-doped tin oxide, antimony-doped tin oxide, zinc oxide, aluminum-doped zinc oxide, indium tin oxide, metal nitride, metal selenide and metal sulfide. The second conductive layer is a cathode and comprises a conductive material. It is preferred that the material has a good thin film-forming property to ensure sufficient contact between the second conductive layer and hole transport layer to promote the electron injection under low voltage and provide better stability. For example, the material of the cathode can be a metal such as aluminum and calcium, a metal alloy such as magnesium/silver and aluminum/lithium, and any combination thereof. Moreover, an extremely thin film of lithium fluoride may be optionally placed between the cathode and the emitting layer. Lithium fluoride can effectively reduce the energy barrier of injecting electrons from the cathode to the emitting layer. In addition, the emitting layer plays a very important role in the whole structure of the light emitting device. In addition to determining the color of the device, the emitting layer also has an important impact on the luminance efficiency in a whole. Common luminescent materials can be classified as fluorescence and phosphorescence depending on the light emitting mechanism.

Definitions

The term "dienophile," refers to a molecule that possesses 2 π-electrons, and which can participate in Diels-Alder cycloaddition reactions. Examples of this include alkenes, alkynes, nitriles, enol ethers, and enamines.

The term "organic electronic device," refers to a device that carries out an electrical operation with the presence of organic materials. Specific example includes organic light emitting devices, organic solar cells, organic memory devices, organic sensors, organic thin film transistors, and power generation and storage devices such as organic batteries, fuel cells, and organic supercapacitors.

The term "organic light emitting device," refers to a device that emits light when an electrical current is applied across two electrodes. Specific example includes light emitting diodes.

The term "polymeric charge transfer layer," refers to a polymeric material that can transport charge carrying moieties, either holes or electrons. Specific example includes hole transport layer.

The term "aromatic moiety," refers to an organic moiety derived from aromatic hydrocarbon by deleting at least one hydrogen atom therefrom. An aromatic moiety may be a monocyclic and/or fused ring system, each ring of which suitably contains from 4 to 7, preferably from 5 or 6 atoms. Structures wherein two or more aromatic moieties are combined through single bond(s) are also included. Specific examples include phenyl, naphthyl, biphenyl, anthryl, indenyl, fluorenyl, benzofluorenyl, phenanthryl, triphenylenyl, pyrenyl, perylenyl, chrysenyl, naphtacenyl, and fluoranthenyl. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl.

The term "heteroaromatic moiety," refers to an aromatic moiety, in which at least one carbon atom or CH group or $CH_2$ group is substituted with a heteroatom or a chemical group containing at least one heteroatom. The heteroaromatic moiety may be a 5- or 6-membered monocyclic heteroaryl, or a polycyclic heteroaryl which is fused with one or more benzene ring(s), and may be partially saturated. The structures having one or more heteroaromatic moieties bonded through a single bond are also included. Specific examples include monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-b]benzothiophenyl, isobenzofuranyl, benzimidazolyl, benzothiazolyl, benzisothiazolyl, benzoxazolyl, benzisoxazolyl, indolyl, isoindolyl, indazolyl, benzothia-diazolyl, quinolyl, isoquinolyl, cinnolinyl, quinazolinyl, quinoxalinyl, carbazolyl, phenanthridinyl and benzodioxolyl.

The term "hydrocarbyl," refers to a chemical group containing only hydrogen and carbon atoms.

The term "substituted hydrocarbyl," refers to a hydrocarbyl in which at least one hydrogen atom is substituted with a heteroatom or a chemical group containing at least one heteroatom.

The term "heterohydrocarbyl," refers to a chemical group containing hydrogen and carbon atoms, and wherein at least one carbon atom or CH group or $CH_2$ group is substituted with a heteroatom or a chemical group containing at least one heteroatom.

The term "substituted heterohydrocarbyl," refers to a heterohydrocarbyl in which at least one hydrogen atom is substituted with a heteroatom or a chemical group containing at least one heteroatom.

The term "aryl," refers to an organic radical derived from aromatic hydrocarbon by deleting one hydrogen atom therefrom. An aryl group may be a monocyclic and/or fused ring system, each ring of which suitably contains from 4 to 7, preferably from 5 or 6 atoms. Structures wherein two or more aryl groups are combined through single bond(s) are also included. Specific examples include phenyl, naphthyl, biphenyl, anthryl, indenyl, fluorenyl, benzofluorenyl, phenanthryl, triphenylenyl, pyrenyl, perylenyl, chrysenyl, naphtacenyl, and fluoranthenyl. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl.

The term "substituted aryl," refers to an aryl in which at least one hydrogen atom is substituted with a heteroatom or a chemical group containing at least one heteroatom.

The term "heteroaryl," refers to an aryl group, in which at least one carbon atom or CH group or $CH_2$ group is substituted with a heteroatom or a chemical group containing at least one heteroatom. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof.

The term "substituted heteroaryl," refers to a heteroaryl in which at least one hydrogen atom is substituted with a heteroatom or a chemical group containing at least one heteroatom.

Heteroatoms include O, N, P, P(=O), Si, B and S.

The term "polymer," refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into and/or within the polymer structure), and the term interpolymer as defined hereinafter.

The term "interpolymer," refers to polymers prepared by the polymerization of at least two different types of monomers. The generic term interpolymer thus includes copolymers (employed to refer to polymers prepared from two different types of monomers), and polymers prepared from more than two different types of monomers.

EXAMPLES

I. Reagents and Test Methods

All solvents and reagents were obtained from commercial vendors, for example, Sigma-Aldrich, TCI, and Alfa Aesar, and were used in the highest available purities, and/or when necessary, recrystallized before use. Dry solvents were obtained from in-house purification/dispensing system (hexane, toluene, and tetrahydrofuran), or purchased from Sigma-Aldrich. All experiments involving "water sensitive compounds" were conducted in "oven dried" glassware, under nitrogen atmosphere, or in a glovebox.

$^1$H-NMR-spectra (500 MHz or 400 MHz) was obtained on a Varian VNMRS-500 or VNMRS-400 spectrometer, at 30° C., unless otherwise noted. The chemical shifts were referenced to tetramethylsilane (TMS, δ=0.00) in $CDCl_3$.

Routine liquid chromatography/mass spectrometry (LC/MS) studies were carried out as follows. One microliter aliquots of the sample, as "1 mg/ml solution in tetrahydrofuran (THF)," were injected on an Agilent 1200SL binary liquid chromatography (LC), coupled to an Agilent 6520 quadruple time-of-flight (Q-TOF) MS system, via a dual electrospray interface (ESI), operating in the PI mode. The following analysis conditions were used: Column: Agilent Eclipse XDB-C18, 4.6*50 mm, 1.7 um; Column oven temperature: 30° C.; Solvent A: THF; Solvent B: 0.1% formic acid in water/Acetonitrile (v/v, 95/5); Gradient: 40-80% Solvent A in 0-6 min, and held for 9 min; Flow: 0.3 mL/min; UV detector: diode array, 254 nm; MS condition: Capillary Voltage: 3900 kV (Neg), 3500 kV (Pos); Mode: Neg and Pos; Scan: 100-2000 amu; Rate: Is/scan; Desolvation temperature: 300° C.

Gel permeation chromatography (GPC) studies were carried out as follows. 2 mg of B-staged HTL polymer was dissolved in 1 mL THF. The solution was filtrated through a 0.20 m polytetrafluoroethylene (PTFE) syringe filter and 50 µl of the filtrate was injected to the GPC system. The following analysis conditions were used: Pump: Waters™ e2695 Separations Modules at a nominal flow rate of 1.0 mL/min; Eluent: Fisher Scientific HPLC grade THF (unstabilized); Injector: Waters e2695 Separations Modules; Columns: two 5 µm mixed-C columns from Polymer Laboratories Inc., held at 40° C.; Detector: Shodex RI-201 Differential Refractive Index (DRI) Detector; Calibration: 17 polystyrene standard materials from Polymer Laboratories Inc., fit to a 3rd order polynomial curve over the range of 3,742 kg/mol to 0.58 kg/mol.

II. Examples

1. Synthesis of N-([1,1'-biphenyl]-4-yl)-9,9-dimethyl-N-(4-(4,4,5,5-tetramethyl-1,3,2-dioxaborolan-2-yl)phenyl)-9H-fluoren-2-amine (Formula 1)

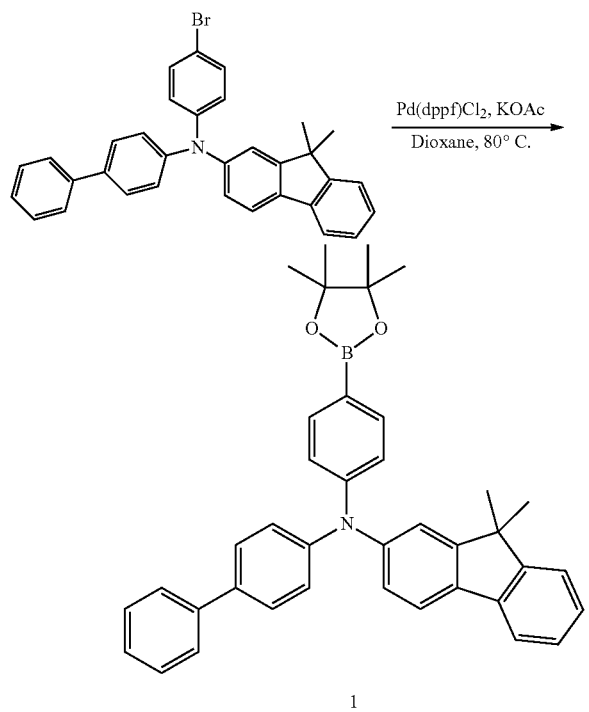

A mixture of N-([1,1'-biphenyl]-4-yl)-N-(4-bromophenyl)-9,9-dimethyl-9H-fluoren-2-amine (15.48 g, 30 mmol), 4,4,4',4',5,5,5',5'-octamethyl-2,2'-bi(1,3,2-dioxaborolane) (9.14 g, 36 mmol), Pd(dppf)$_2$Cl$_2$ (571 mg, 0.75 mmol), CH$_3$COOK (4.41 g, 45 mmol), and 60 mL of dry dioxane were heated at 85° C. under nitrogen atmosphere for 12 h. After cooling to room temperature, solvent was removed under vacuum and then water was added. The mixture was extracted with CH$_2$Cl$_2$. The organic phase was collected and dried over anhydrous sodium sulphate. After filtration, the filtrate was evaporated to remove solvent and the residue was purified through column chromatography on silica gel to give white solid (84% yield). The product had the following characteristic: MS (ESI): 564.30 [M+H]$^+$. $^1$H-NMR (CDCl$_3$, 400 MHz, TMS, ppm): δ 7.65 (d, 2H), 7.59 (d, 2H), 7.50 (d, 2H), 7.40 (m, 8H), 7.17 (m, 3H), 7.05 (m, 3H), 1.42 (s, 6H), 1.38 (s, 12H).

2. Synthesis of 9-(4-formylphenyl)-9H-carbazole-3-carbaldehyde (Formula 2)

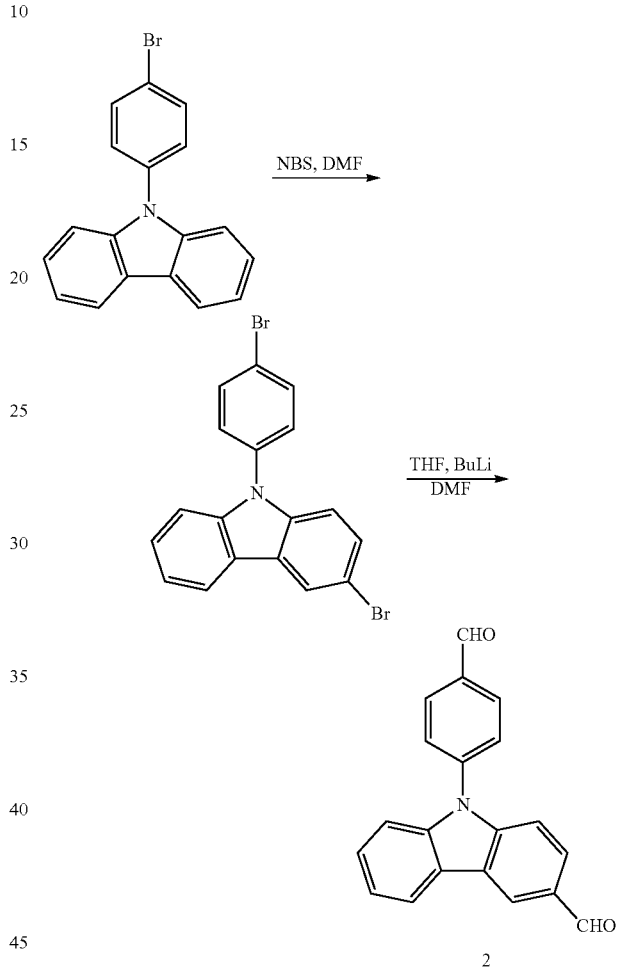

To a solution of 9-(4-bromophenyl)-9H-carbazole (32.2 g, 100 mmol) in 150 mL dimethyl formamide (DMF), N-bromosuccinimide (NBS) (17.8 g, 100 mmol) in 100 mL DMF was added dropwise in 30 min. After addition, the mixture was stirred at room temperature for 12 h and then poured into water to precipitate. The solid was filtrated and recrystallized from dichloromethane and ethanol to give white solid (92% yield) and used for the next step. The product had the following characteristic: MS (ESI): 402.09 [M+H]$^+$.

To a solution of 3-bromo-9-(4-bromophenyl)-9Hcarbazole (8.02 g, 20 mmol) in THF (500 mL), n-BuLi (24 mL of a 2.5M solution in hexanes, 60 mmol) was added at a rate to keep the internal temperature below −78° C. The mixture was stirred at −78° C. for 1 h and 10 mL DMF with 10 mL THF were added dropwise. After the addition, the reaction mixture was stirred at −45° C. for 30 min and at 0° C. for an additional 30 min. Saturated aqueous NH$_4$Cl (400 mL) was added and the organic solvent was evaporated. The residue was extracted with CH$_2$Cl$_2$ (2×100 mL) and the combined organic phase was dried over anhydrous MgSO$_4$. After removing solvent, the crude product was purified through column chromatography to give crude product (65% yield).

The product had the following characteristics: MS (ESI): 300.09 [M+H]⁺. ¹H-NMR (CDCl₃, 400 MHz, TMS, ppm): δ 10.15 (s, 1H), 10.13 (s, 1H), 8.67 (s, 1H), 8.23 (d, 1H), 8.17 (d, 2H), 7.99 (d, 1H), 7.80 (d, 2H), 7.54 (m, 3H), 7.40 (m, 1H).

3. Synthesis of 6-bromo-9-(4-formylphenyl)-9H-carbazole-3-carbaldehyde (Formula 3)

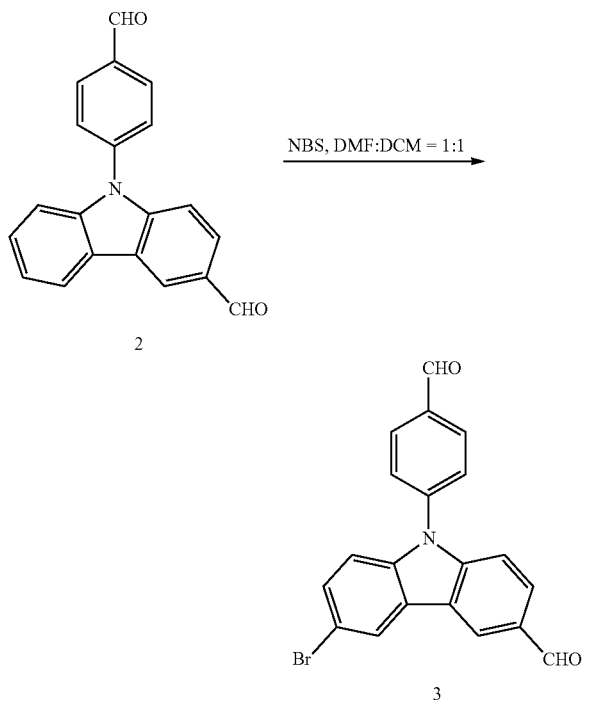

To a solution of Formula 2 chemical (0.898 g, 3 mmol) in CH₂Cl₂ (20 mL) and DMF (20 mL), NBS (0.587 mg, 3.3 mmol) was added in portion. After stirred for 4 h, the precipitates formed was filtered and washed with DMF and CH₂Cl₂ for several times to afford the crude product (84% yield). The product had the following characteristic: MS (ESI): 378.01 [M+H]⁺. (Fail to get ¹H-NMR data due to low solubility).

4. Synthesis of 6-(4-(1,1'-biphenyl-4-yl(9,9-dimethyl-9H-fluoren-2-yl)amino)phenyl)-9-(4-formylphenyl)-9H-carbazole-3-carbaldehyde (Formula 4)

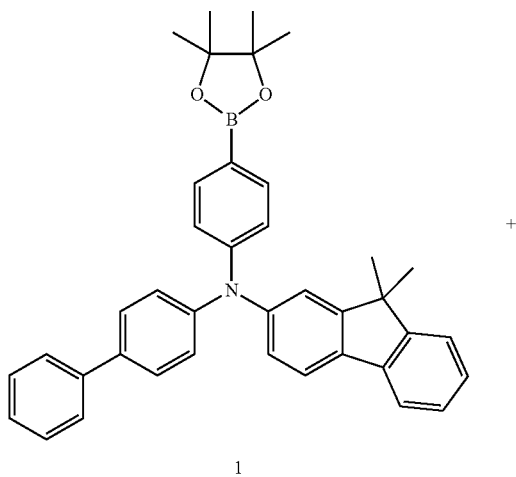

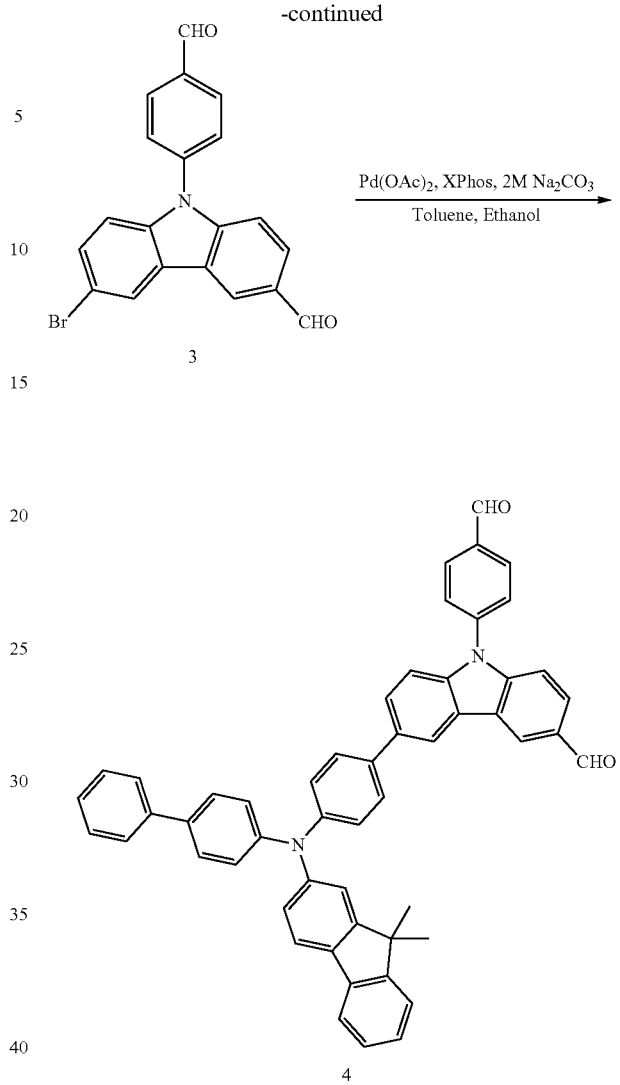

To a mixture of Formula 3 chemical (0.756 g, 2 mmol), Formula 1 chemical (1.24 g, 2.2 mmol), Pd(OAc)₂ (12.8 mg, 0.06 mmol) and X-Phos (28.6 mg, 0.06 mmol), 20 mL mixed solvents with proportion of 1:1:2 mixture of 2.0M Na₂CO₃: Ethanol:toluene were added under flow of nitrogen. The reaction mixture was stirred overnight under nitrogen atmosphere at 90° C. After evaporation of toluene and ethanol, water was added and the mixture was extracted with CH₂Cl₂ (2×30 mL) and the combined organic phase was dried over MgSO₄. The solvent was removed under reduced pressure and the residue was purified through column chromatography on silica gel to give yellow solid (64% yield). The product had the following characteristics: MS (ESI): 735.29 [M+H]+. ¹H-NMR (CDCl₃, 400 MHz, TMS, ppm): δ 10.12 (s, 1H), 10.09 (s, 1H), 8.36 (s, 1H), 8.20 (d, 1H), 7.64 (m, 12H), 7.53 (m, 2H), 7.42 (m, 6H), 7.32 (m, 7H), 7.15 (d, 1H), 4.88 (s, 2H), 4.85 (s, 2H), 1.45 (s, 6H).

5. Synthesis of (4-(3-(4-([1,1'-biphenyl]-4-yl(9,9-dimethyl-9H-fluoren-2-yl)amino)phenyl)-6-(hydroxymethyl)-9H-carbazol-9-yl)phenyl)methanol (Formula 5)

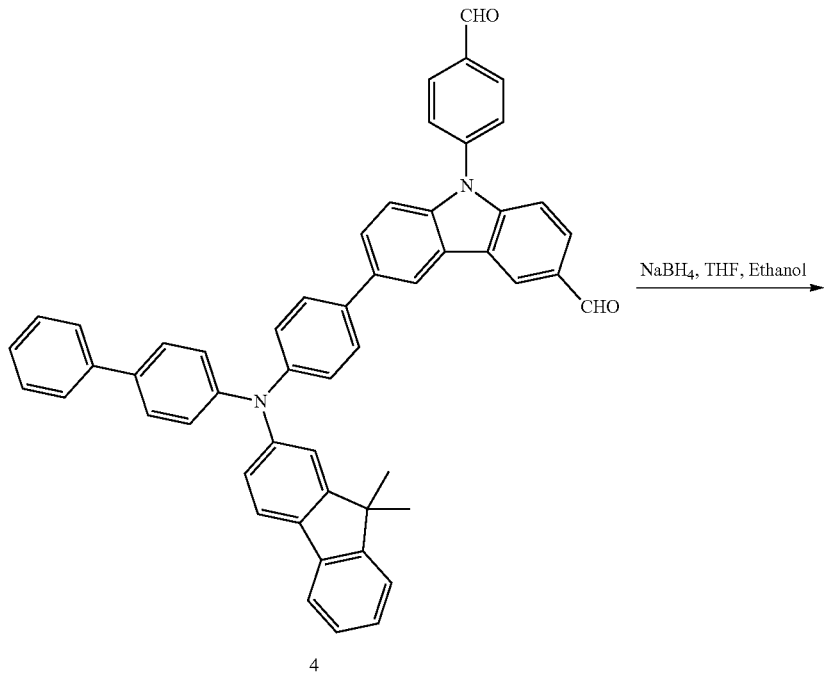

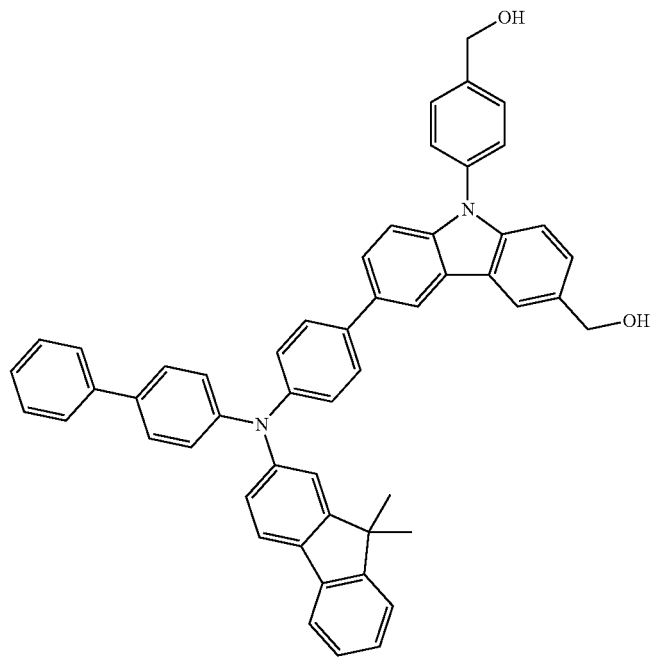

To a solution of Formula 4 chemical (734 mg, 1 mmol) in 10 mL THF and 10 mL ethanol at 40° C., NaBH$_4$ (302 mg, 8 mmol) was added under nitrogen atmosphere. The solution was allowed to stir at room temperature for 2 h. Then, aqueous hydrochloric acid solution was added until pH 5 and the mixture was kept stirring for 30 min. The solvent was removed under vacuum and the residue was extracted with dichloromethane. The product was then dried under vacuum and used for the next step without further purification (95% yield). The product had the following characteristics: MS (ESI): 739.32 [M+H]$^+$. $^1$H-NMR (CDCl$_3$, 400 MHz, TMS, ppm): δ 8.36 (s, 1H), 8.20 (d, 1H), 7.64 (m, 12H), 7.53 (m, 2H), 7.42 (m, 6H), 7.32 (m, 7H), 7.15 (d, 1H), 4.88 (s, 2H), 4.85 (s, 2H), 3.74 (m, 2H), 1.45 (s, 6H).

6. Synthesis of Monomer B chemical, N-([1,1'-biphenyl]-4-yl)-9,9-dimethyl-N-(4-(6-(((4-vinylbenzyl)oxy)methyl)-9-(4-(((4-vinylbenzyl)oxy)methyl)phenyl)-9H-carbazol-3-yl)phenyl)-9H-fluoren-2-amine (99.6% purity)

To a solution of Formula 5 chemical (3.69 g, 5 mmol) in 50 mL dry DMF was added NaH (432 mg, 18 mmol), the mixture was stirred at room temperature for 1 h. And 1-(chloromethyl)-4-vinylbenzene (2.75 g, 15 mmol) was added to above solution via syringe. The mixture was heated

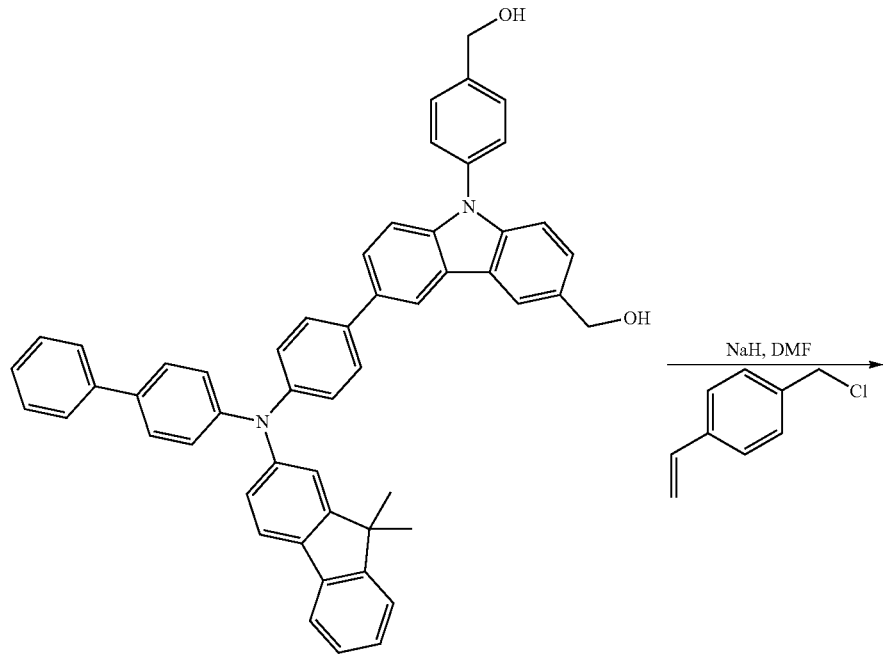

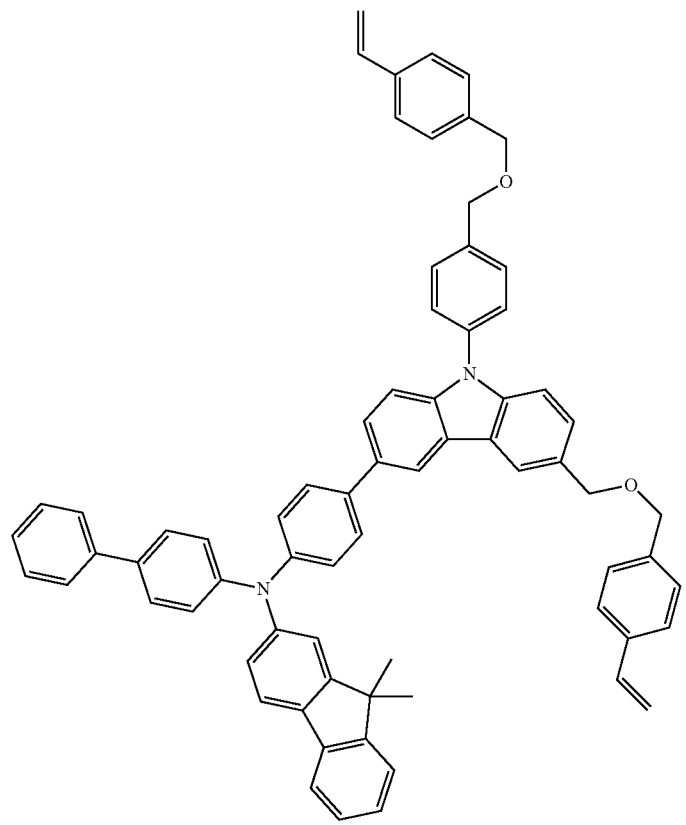

Monomer B4 to 60° C. overnight. After quenched with water, the mixture was poured into water to remove DMF. The residue was filtrated and the resulting solid was dissolved with dichloromethane, which was then washed with water. The solvent was removed under vacuum and the residue was extracted with dichloromethane. The product was then obtained by column chromatography on silica gel (55% yield). The product had the following characteristics: MS (ESI): 943.42 [M+H]$^+$. $^1$H-NMR (CDCl$_3$, 400 MHz, TMS, ppm): δ 8.35 (s, 1H), 8.17 (d, 1H), 7.62 (m, 12H), 7.42 (m, 14H), 7.29 (m, 10H), 6.72 (dd, 2H), 5.77 (d, 2H), 5.24 (d, 2H), 4.74 (s, 2H), 4.67 (s, 4H), 4.60 (s, 2H), 1.45 (s, 6H).

7. Synthesis of Monomer A chemical, N-([1,1'-biphenyl]-4-yl)-N-(4-(6-((bicyclo[4.2.0]octa-1(6),2,4-trien-7-yloxy)methyl)-9-(4-((bicyclo[4.2.0]octa-1(6),2,4-trien-7-yloxy)methyl)phenyl)-9H-carbazol-3-yl)phenyl)-9,9-dimethyl-9H-fluoren-2-amine (99.6% purity)

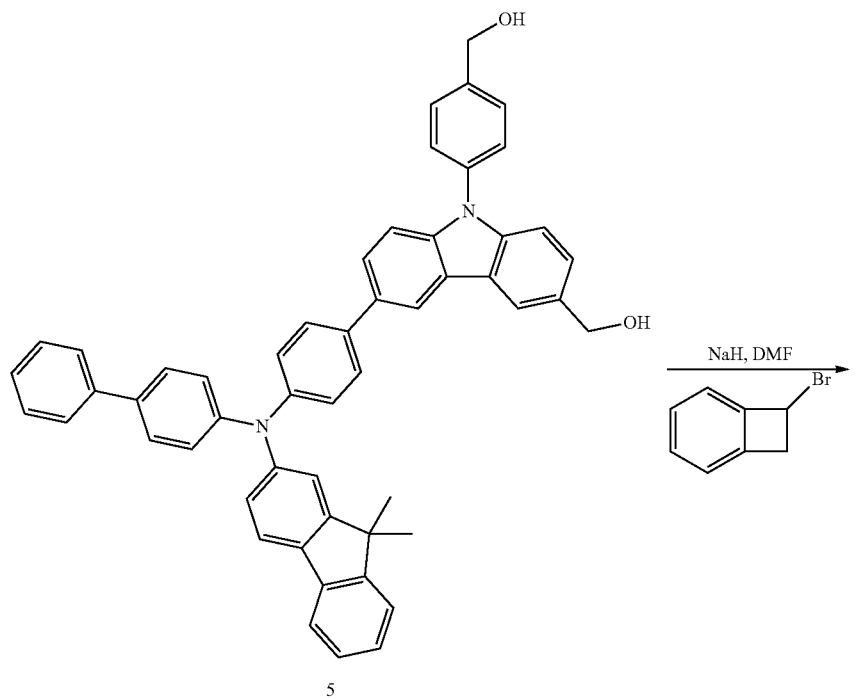

5

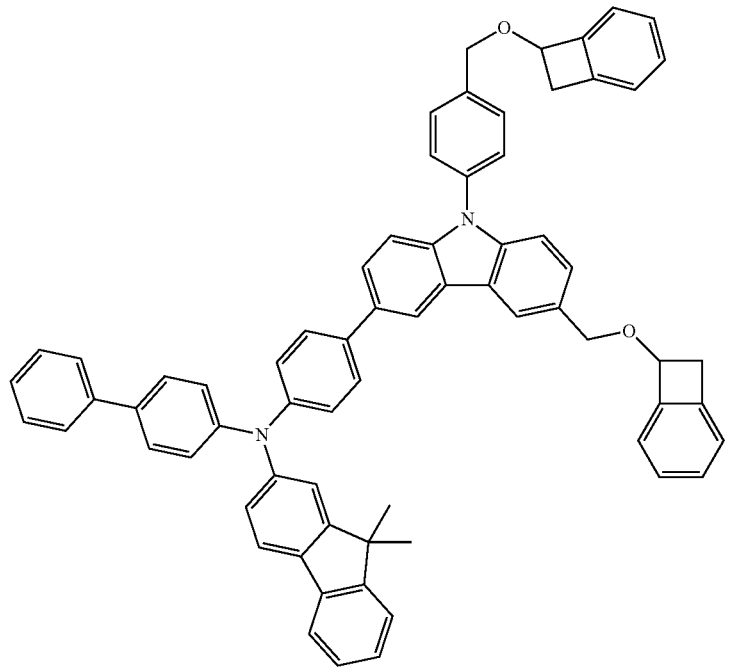

Monomer A24

To a solution of Formula 5 chemical (3.69 g, 5 mmol) in 50 mL dry DMF was added NaH (432 mg, 18 mmol), the mixture was stirred at room temperature for 1 h. And 7-bromobicyclo[4.2.0]octa-1,3,5-triene (Br-BCB) (2.75 g, 15 mmol) was added to above solution via syringe. The mixture was heated to 60° C. and stirred overnight. After quenched with water, the mixture was poured into water to remove DMF. The residue was filtrated and the resulting solid was dissolved with dichloromethane, which was then washed with water. The solvent was removed under vacuum and the residue was extracted with dichloromethane. The product was then obtained by column chromatography on silica gel (65% yield). The product had the following characteristics: MS (ESI): 943.42 $[M+H]^+$. $^1$H-NMR ($CDCl_3$, 400 MHz, TMS, ppm): δ 8.35 (s, 1H), 8.22 (d, 1H), 7.65 (m, 12H), 7.47 (d, 2H), 7.43 (m, 6H), 7.29 (m, 10H), 7.15 (m, 6H), 5.27 (d, 2H), 4.89 (s, 2H), 4.82 (s, 2H), 3.55 (d, 2H), 3.22 (d, 2H), 1.45 (s, 6H).

8. B-Staged HTL Polymer Preparation

A mixture of Monomer A chemical (Monomer A24, 657.1 mg, 0.697 mmol), Monomer B chemical (Monomer B4, 479.7 mg, 0.494 mmol), and tris(4'-vinyl-[1,1'-biphenyl]-4-yl)amine (Monomer C6) (72.7 mg, 0.132 mmol, 99.6% purity) was dissolved in 1.2 mL electronic anisole to make a 10 wt % solution. The B-staging of the above solution was carried out at 105° C. for 5 hr under nitrogen atmosphere. After cooling to room temperature, the B-staged HTL solution was diluted to 4 wt % with electronic solvent. Equal volume of electronic methanol was then added into the diluted B-staged HTL solution for precipitating HTL polymer out of the solution. The B-staged HTL polymer was then collected via filtration and dried in vacuum oven at 40° C. overnight. The resulting B-staged HTL polymer was re-dissolved in electronic anisole to make a 4 wt % solution and the above precipitation was repeated once more to completely remove residual HTL monomer. Finally, 0.71 g (59% yield) B-staged HTL polymer product was collected in the form of yellow crystalline-like solid. Table 1 showed the B-staged HTL polymer molecular weights and distributions before and after precipitation. It is worthwhile to note that the molecular weight distributions of the B-staged HTL polymer were very broad ranging from $2\times10^3$ g/mol (dimer) to $1\times10^6$ g/mol.

TABLE 1

Molecular weights of B-staged HTL polymer

| Description (g/mol) | $M_n$ | $M_w$ | $M_z$ | $M_{z+1}$ | $M_w/M_n$ |
|---|---|---|---|---|---|
| Initial B-staged polymer | 2,315 | 6,973 | 18,812 | 31,263 | 3.012 |
| $1^{st}$ precipitation | 3,513 | 9,774 | 39,049 | 154,783 | 2.782 |
| $2^{nd}$ precipitation | 4,243 | 16,001 | 155,113 | 437,472 | 3.771 |

9. Light Emitting Device Fabrication

Indium tin oxide (ITO) glass substrates (2*2 cm) were cleaned with solvents ethanol, acetone, and isopropanol by sequence, and then were treated with a UV Ozone cleaner for 15 min. The hole injection layer (HIL) material Plexcore™ OC AQ-1200 from Plextronics Company was spin-coated from water solution onto the ITO substrates in glovebox and annealed at 150° C. for 20 min. After that, for comparative evaporative HTL, N-([1,1'-biphenyl]-4-yl)-9,9-dimethyl-N-(4-(9-phenyl-9H-carbazol-3-yl)phenyl)-9H-fluoren-2-amine, the substrate was transferred into a thermal evaporator for the deposition of the HTL, emitting materials layer (EML), electron transfer layer (ETL) and cathode; for inventive HTL for solution process, HTL materials (B-staged HTL polymers) were deposited from anisole solution and annealed at 150° C. for 10 min to remove organic solvent. After that, the crosslinking of B-staged material was carried out on a hotplate in glovebox at 205° C. for 5 min. Then subsequent phosphorescent green (Ph-Green) EML, ETL and cathode were deposited in sequence. Finally these devices were hermetically sealed prior to testing.

To evaluate electroluminescent (EL) performances of the B-staged polymer as hole-transporting layer material, OLED devices with the following structures were fabricated:

Device A: ITO/AQ-1200/Comparative HTL (evaporated, 800 Å)/EML/ETL/A1;

Device B: ITO/AQ-1200/B-staged HTL (not crosslinked, 400 Å)/EML/ETL/A1;

Device C: ITO/AQ-1200/B-staged HTL (crosslinked, 390 Å)/EML/ETL/A1;

Device D: ITO/AQ-1200/B-staged HTL with 10% p-dopant (crosslinked, 290 Å)/EML/ETL/A1.

The thicknesses of HIL (AQ-1200), EML, ETL and cathode A1 are 470, 400, 350 and 800 Å, respectively.

III. Results

The current-voltage-luminance (J-V-L) characterizations for the OLED devices, that is, driving voltage (V), luminance efficiency (Cd/A), and international commission on illumination (CIE) data at 1000 nit and 50 mA/cm² luminance, and lifetime at 15000 nit for 10 hr were performed with a Keithly™ 238 High Current Source-Measurement Unit and a CS-100A Color and Luminance Meter from Konica Minolta Company and were listed in Table 2. Electroluminescence (EL) spectra of the OLED devices were collected by a calibrated CCD spectrograph and were fixed at 516 nm for all the four OLED device examples.

Device A was fabricated with evaporative Comparative HTL, while Device D was deposited with the inventive B-staged HTL polymer comprising a p-dopant component (trityl tetrakis(pentafluorophenyl)borate from Acros Company) through a solution process. Device B or C was deposited with non-crosslinked B-staged HTL polymer or crosslinked B-staged HTL polymer respectively, without comprising the p-dopant component. Device D, compared to Devices B and C, had a higher lifetime (from 60.2% and 79.2% to 95.8%), which demonstrated the critical role played by the p-dopant component in the HTL polymer. Device C, compared to Device B, had also a higher lifetime (from 79.2% to 95.8%), and demonstrated the critical role played by the Monomer C crosslinking agent.

It should be noted that the by adding the p-dopant component and the crosslinking agent of the present invention, the solution process deposited OLED device performance, in detail, the device lifetime was significantly improved, and was very close to that of evaporative device (Device A).

TABLE 2

| | OLED J-V-L characterizations | | | | | |
|---|---|---|---|---|---|---|
| | V | | | | | |
| Devices | 1000 nit | 50 mA/cm² | Cd/A | CIE | Lifetime | EL |
| A | 3.0/5.0 | | 46.9 | 293, 657 | 97.2% | 516 nm |
| B | 3.6/6.4 | | 50.8 | 292, 656 | 60.2% | 516 nm |
| C | 3.8/6.6 | | 50.6 | 292, 656 | 79.2% | 516 nm |
| D | 3.6/6.4 | | 49.5 | 295 653 | 95.8% | 516 nm |

What is claimed is:
1. A polymeric charge transfer layer formed from a composition comprising, from 1 wt % to 20 wt % based on total weight of the composition, a p-dopant component; and a polymer comprising, as polymerized units, Monomer A, and Monomer C crosslinking agent; wherein Monomer A is selected from the following A13 through A28:
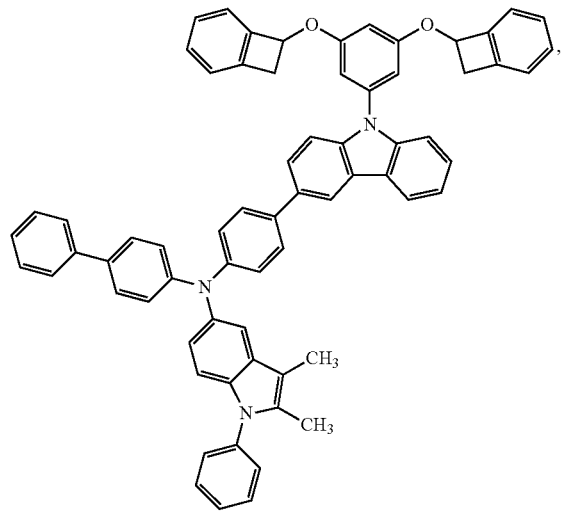
A13)
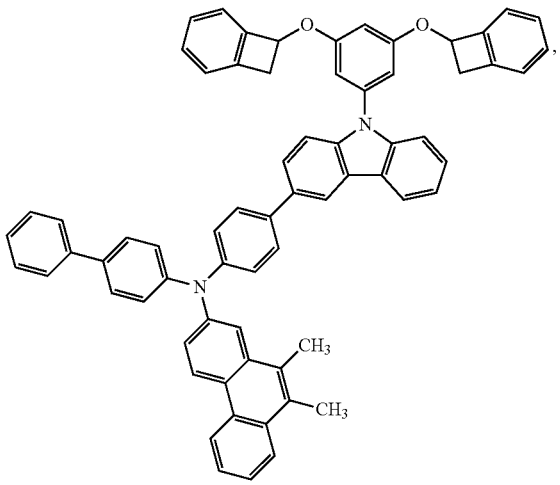
A14)
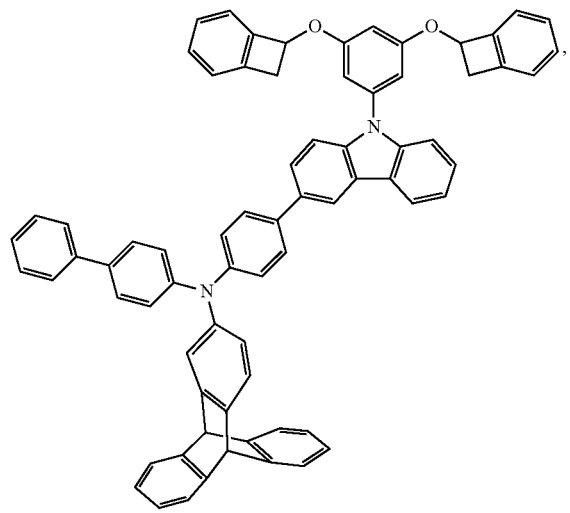
A15)
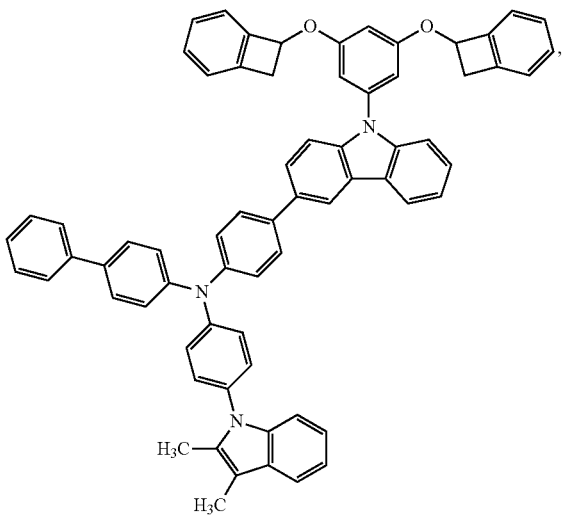
A16)

-continued
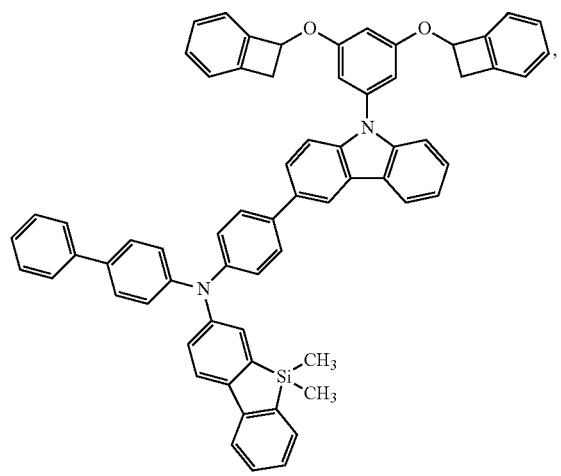
A17)
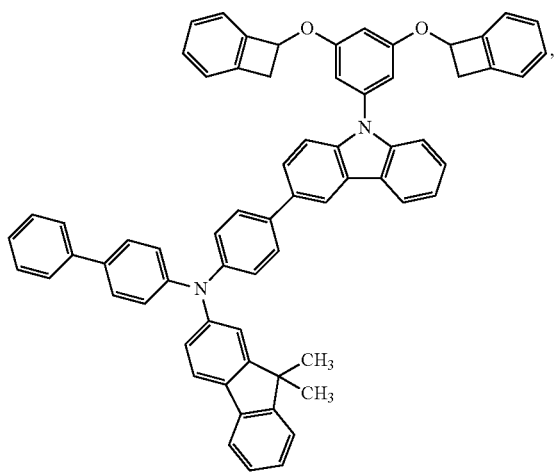
A18)
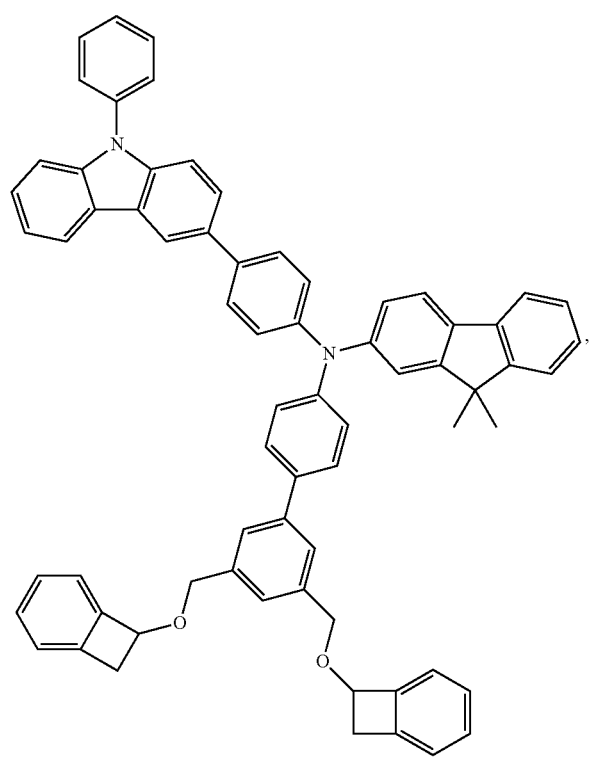
A19)

A20)
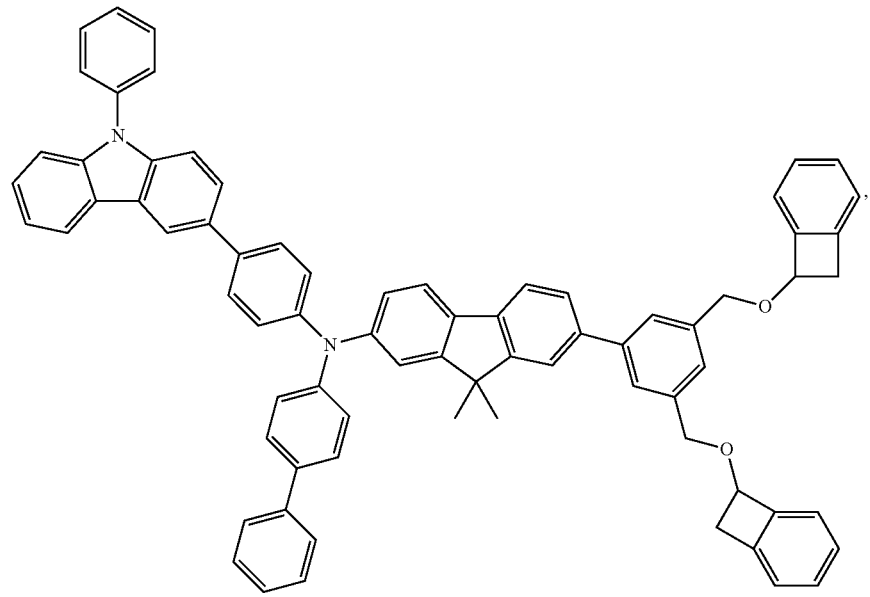
A21)
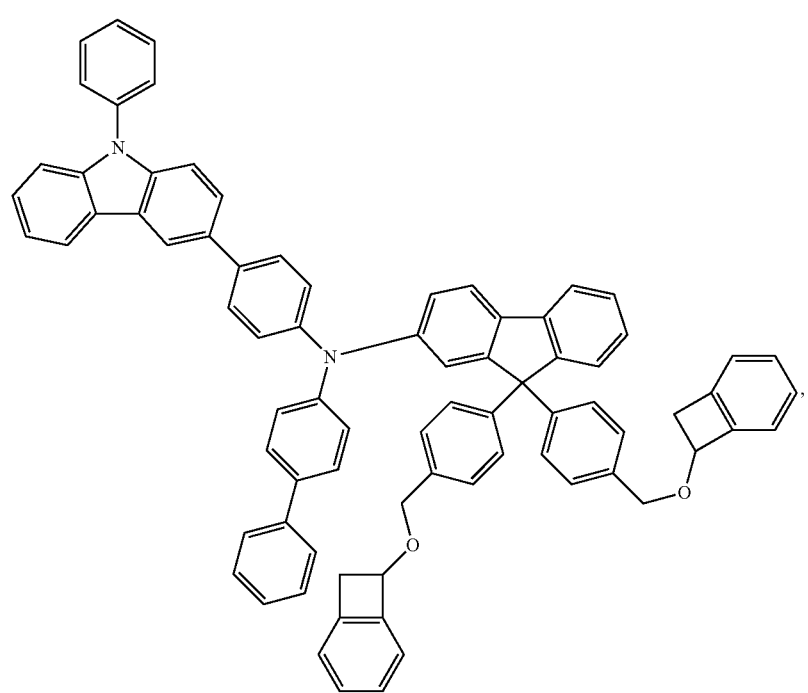

-continued
A22)
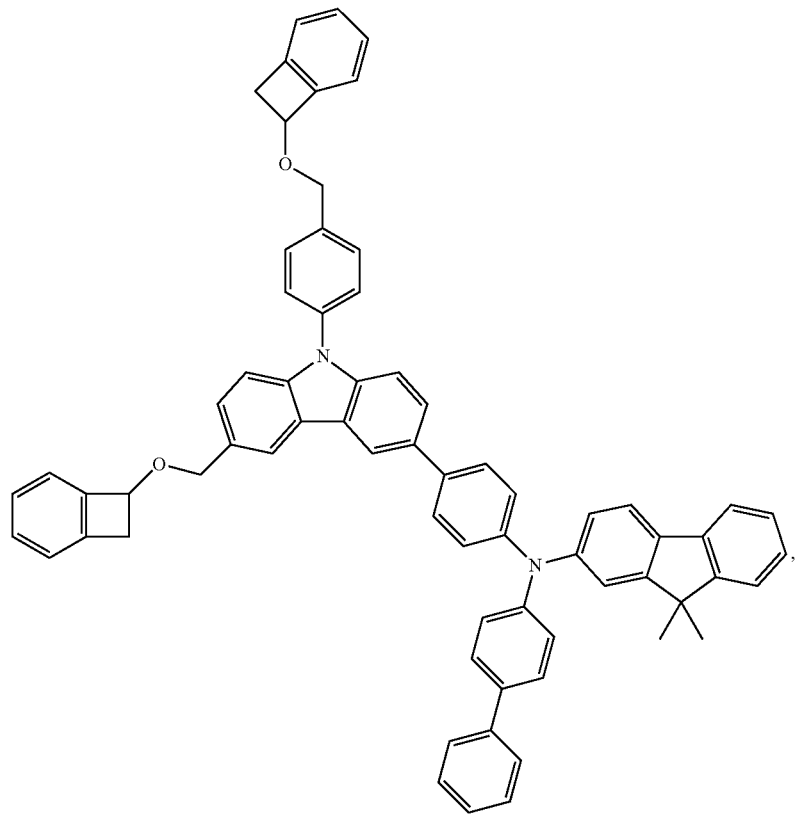
A23)
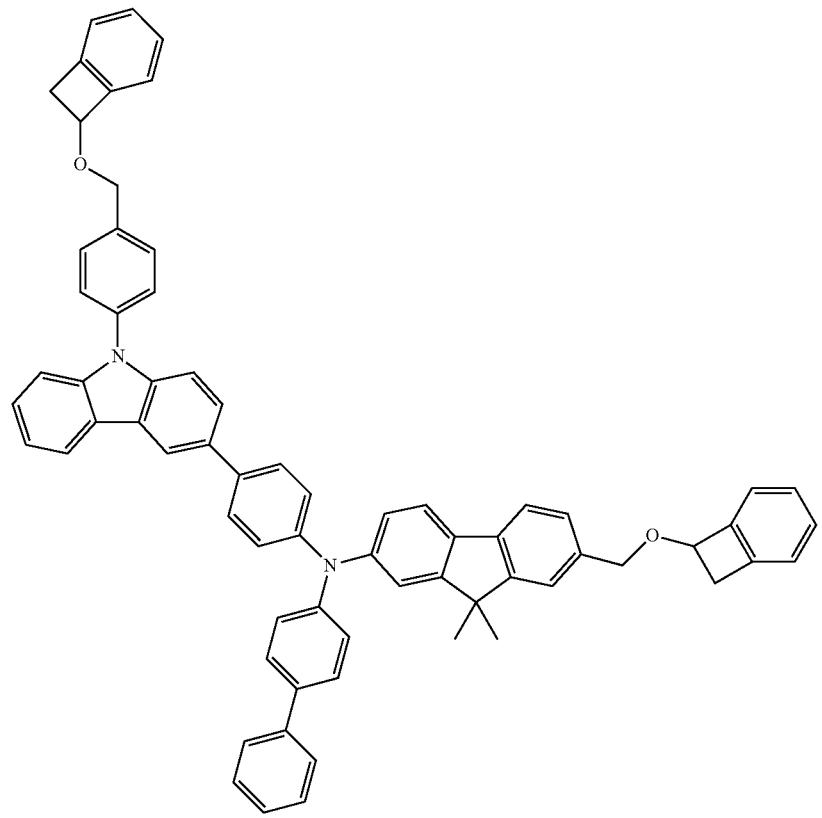

-continued
A24)
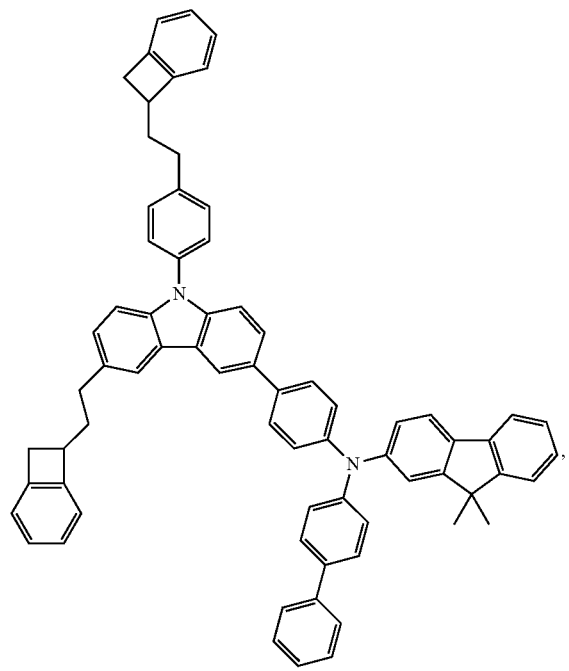
A25)
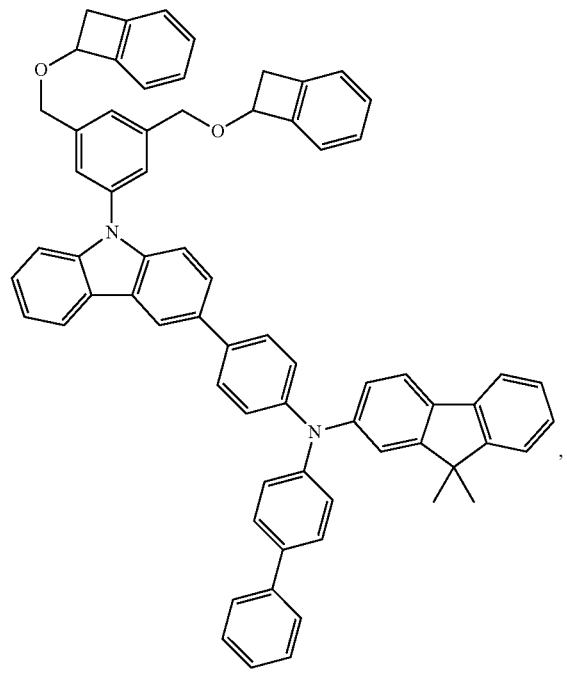
A26)
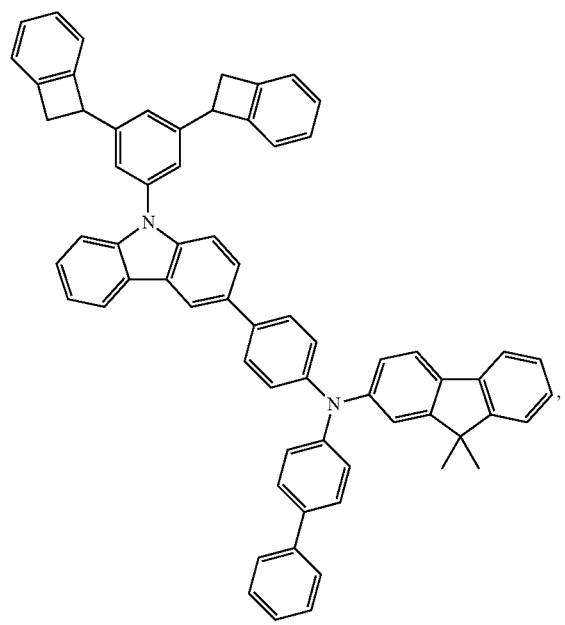
A27)
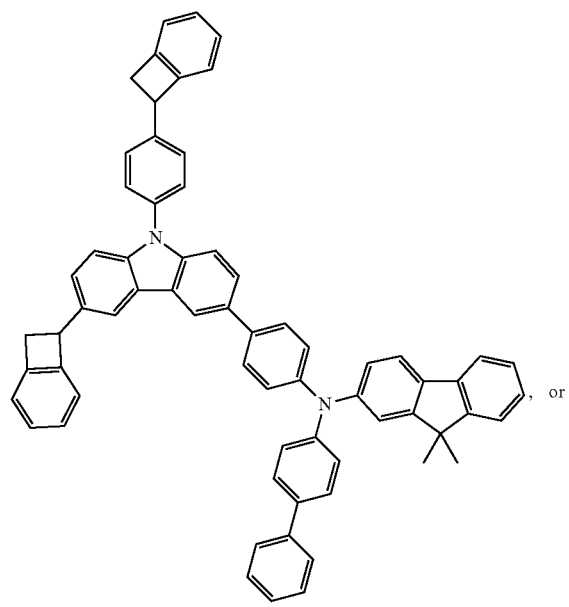
or

A28)

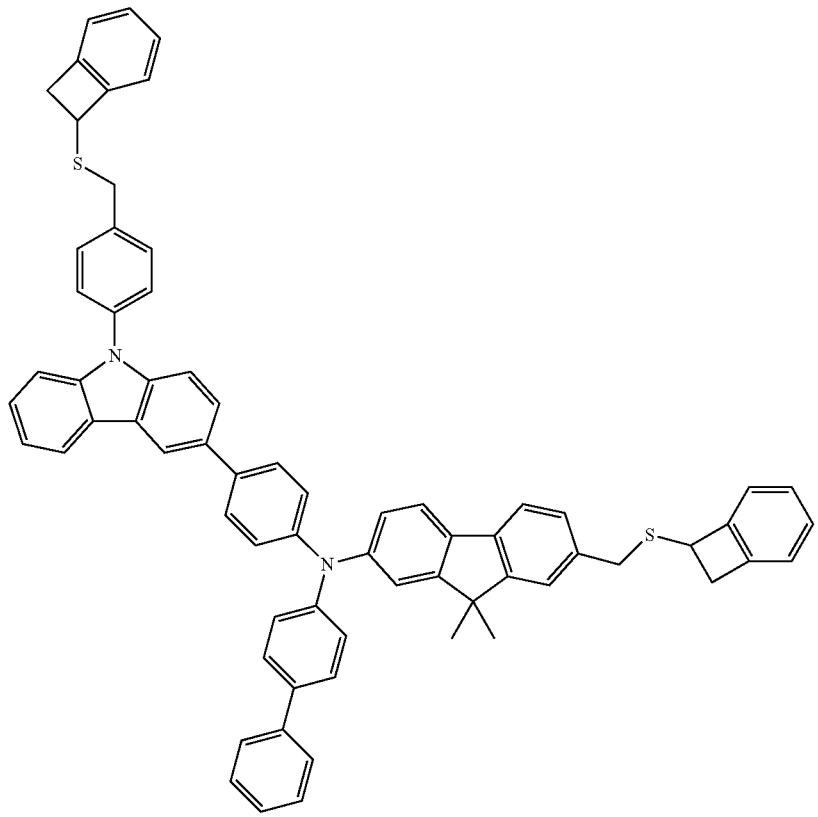

and

Monomer C crosslinking agent has Structure C:

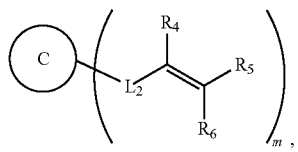

(Structure C)

wherein C is an aromatic moiety, a heteroaromatic moiety, a $C_1$-$C_{50}$ hydrocarbyl, a $C_1$-$C_{50}$ substituted hydrocarbyl, a $C_1$-$C_{50}$ heterohydrocarbyl, or a $C_1$-$C_{50}$ substituted heterohydrocarbyl; and wherein $R_4$ through $R_6$ are each independently selected from the following: hydrogen, deuterium, a $C_1$-$C_{50}$ hydrocarbyl, a $C_1$-$C_{50}$ substituted hydrocarbyl, a $C_1$-$C_{50}$ heterohydrocarbyl, a $C_1$-$C_{50}$ substituted heterohydrocarbyl, halogen, cyano, a $C_5$-$C_{50}$ aryl, a $C_5$-$C_{50}$ substituted aryl, a $C_5$-$C_{50}$ heteroaryl, a $C_5$-$C_{50}$ substituted heteroaryl; and wherein $L_2$ is selected from a heteroatom, an aromatic moiety, a heteroaromatic moiety, a $C_1$-$C_{100}$ hydrocarbyl, a $C_1$-$C_{100}$ substituted hydrocarbyl, a $C_1$-$C_{100}$ heterohydrocarbyl, or a $C_1$-$C_{100}$ substituted heterohydrocarbyl; and wherein m is from 2 to 25; and wherein each chemical group of $L_2$ is independently bonded to C; and wherein two or more of $R_4$ through $R_6$ may optionally form one or more ring structures; and the p-dopant is selected from tropylium salts, imidazolium salts, and trityl salts.

2. The polymeric charge transfer layer according to claim 1, wherein Monomer C crosslinking agent is selected from the following C1-C11:

C1)

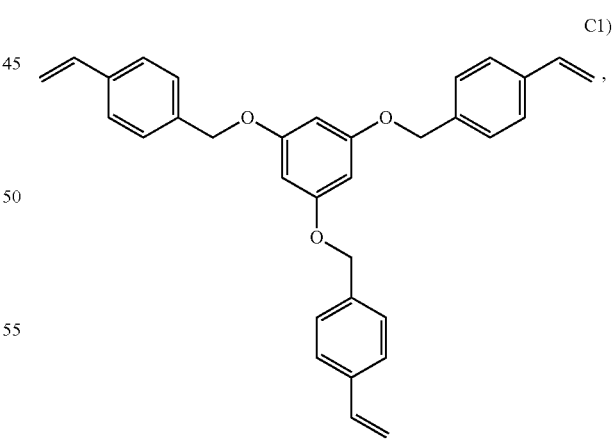

C2)

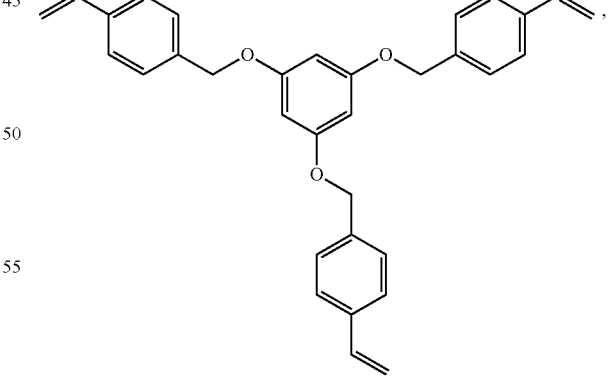

C3)
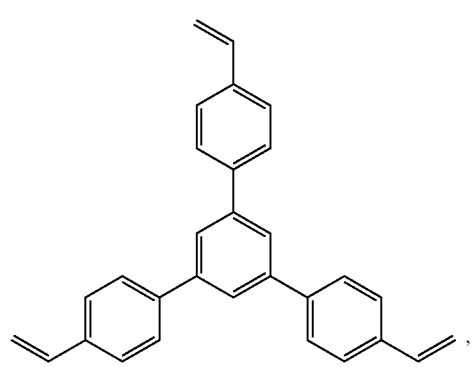
C4)
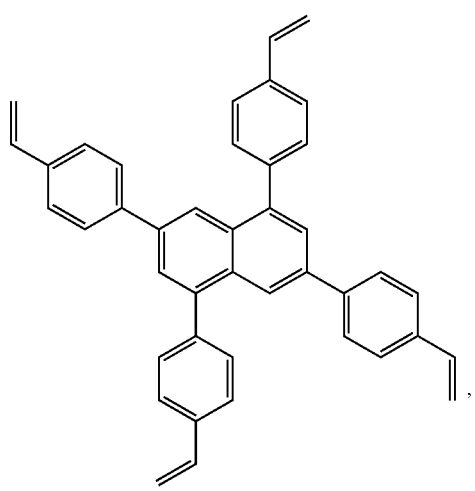
C5)
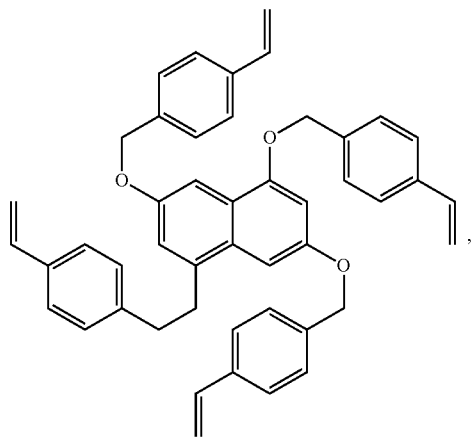
C6)
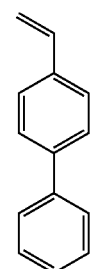
C7)
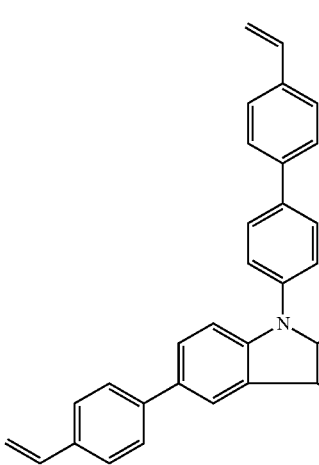

C8) 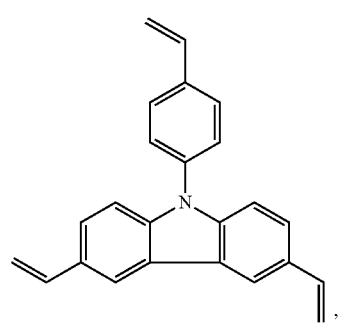
C10) 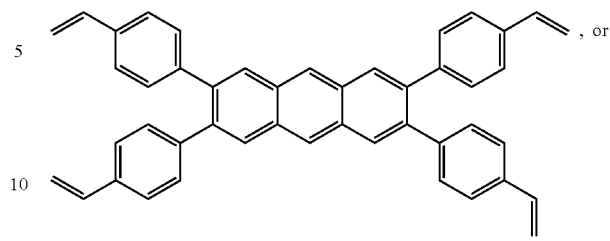, or
C9) 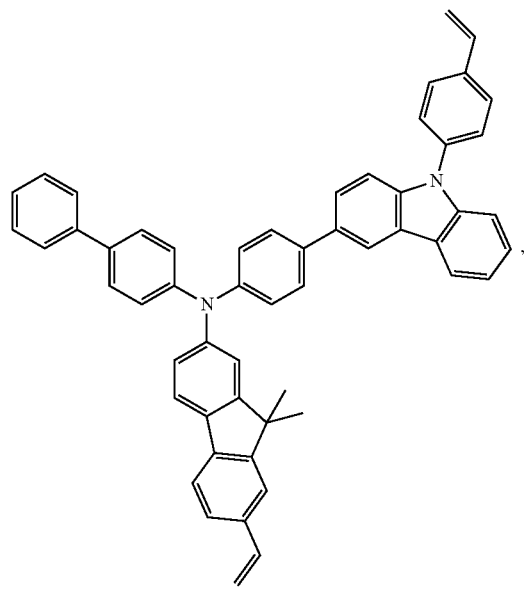
C11) 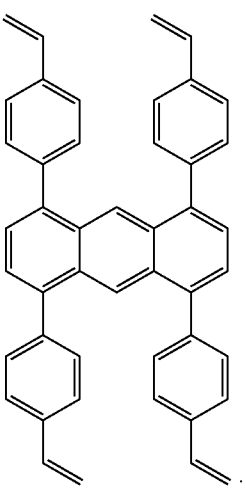
3. The polymeric charge transfer layer according to claim 1 wherein the polymer further comprises Monomer B selected from the following B1 through B6:
B1)
B2)
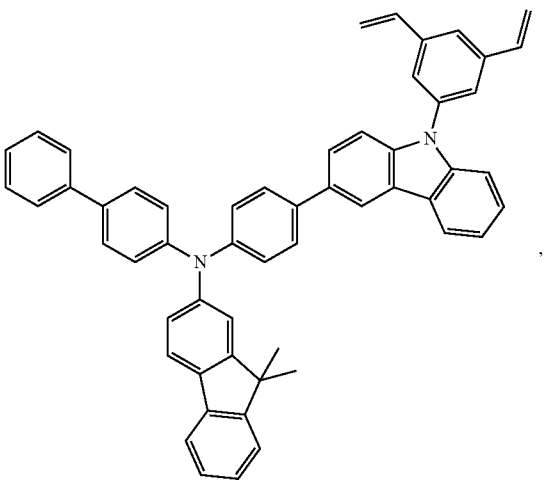

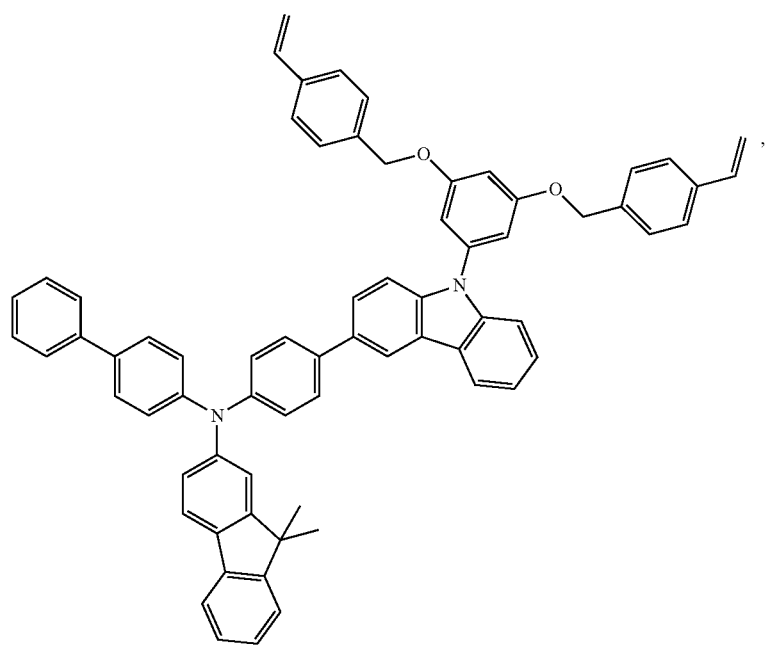
B3)
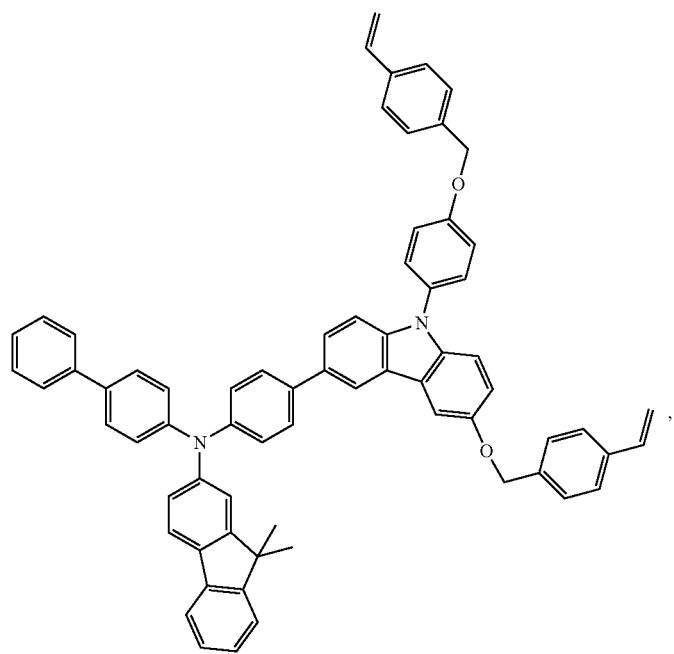
B4)

-continued

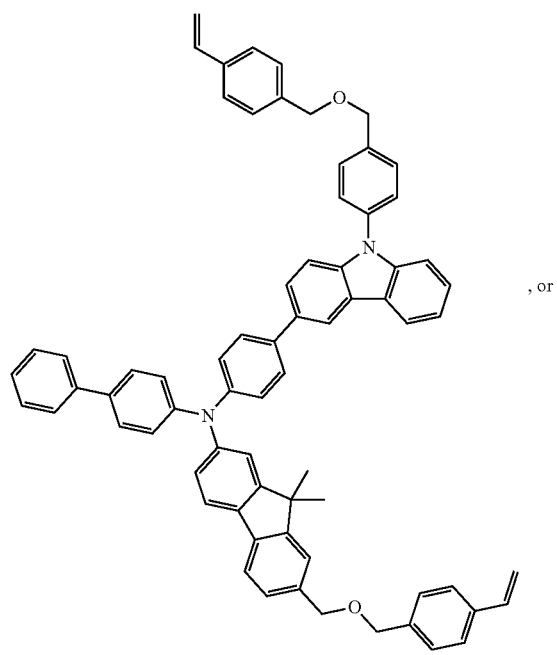
B5)

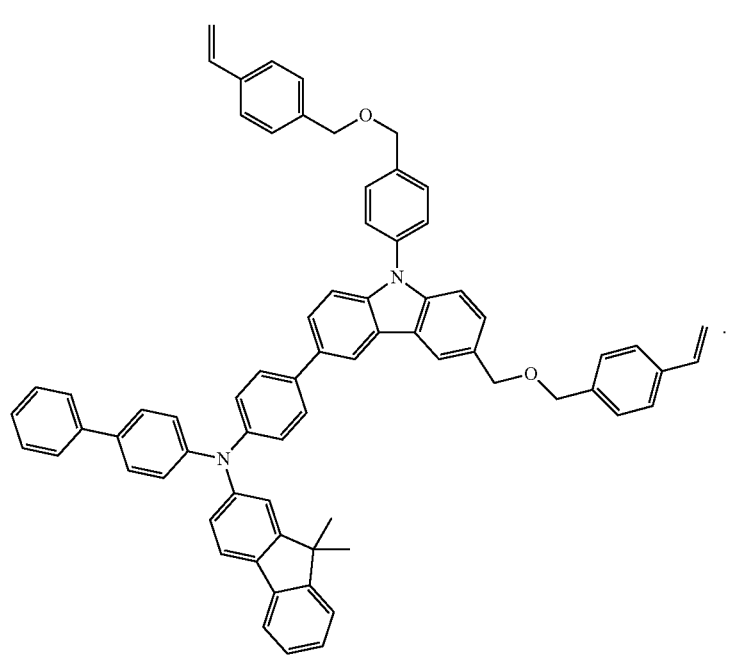
B6)

4. The polymeric charge transfer layer according to claim 1 wherein Monomer C crosslinking agent is from 0.1 to 50 mole % based on the sum moles of Monomer A.

5. The polymeric charge transfer layer according to claim 3, wherein the molar ratio of Monomer A to Monomer B is from 0.8 to 1.2.

6. The polymeric charge transfer layer according to claim 1, wherein the p-dopant has a structure selected from one of the following:

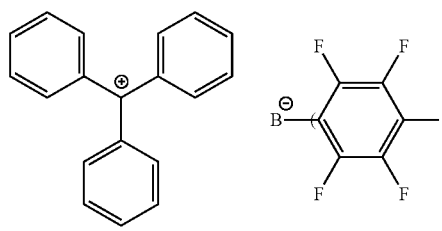

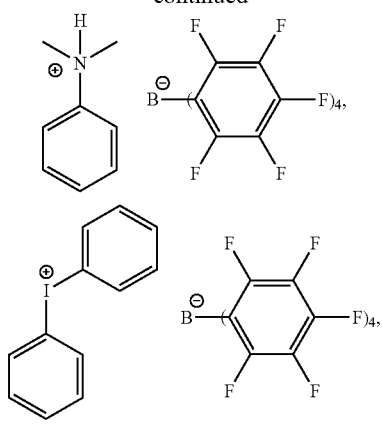
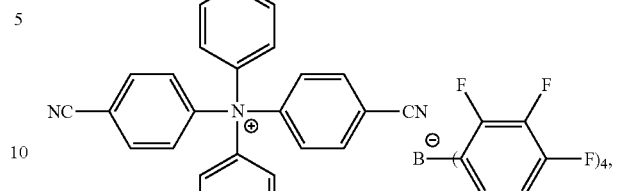
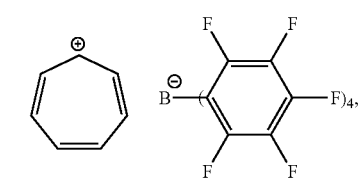
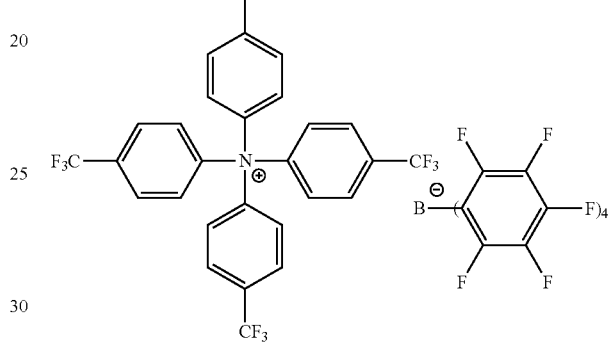
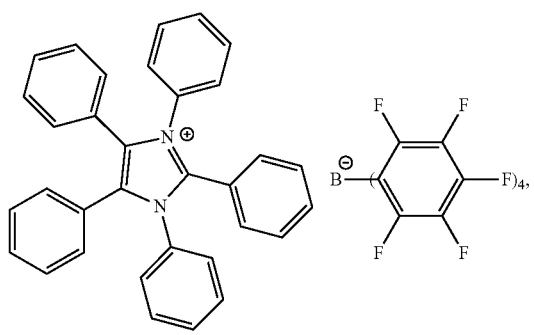
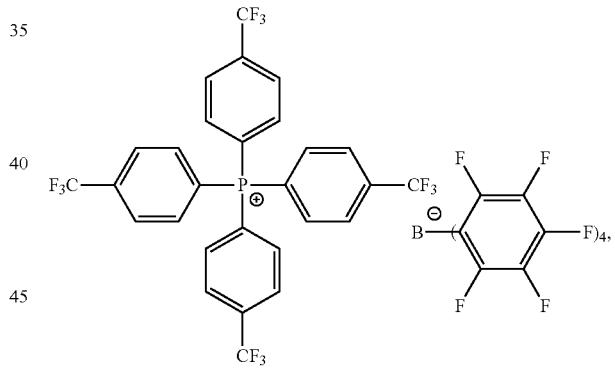
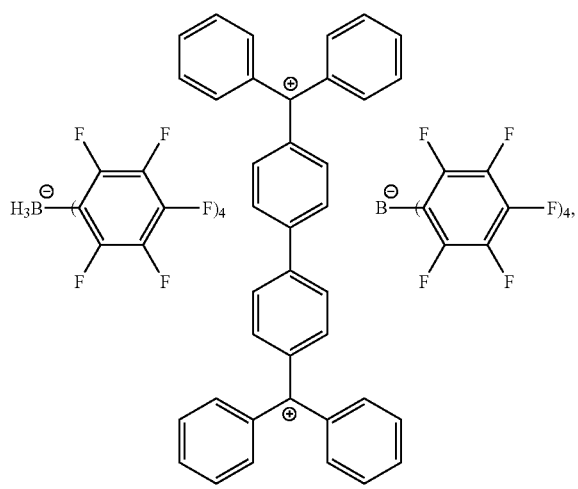
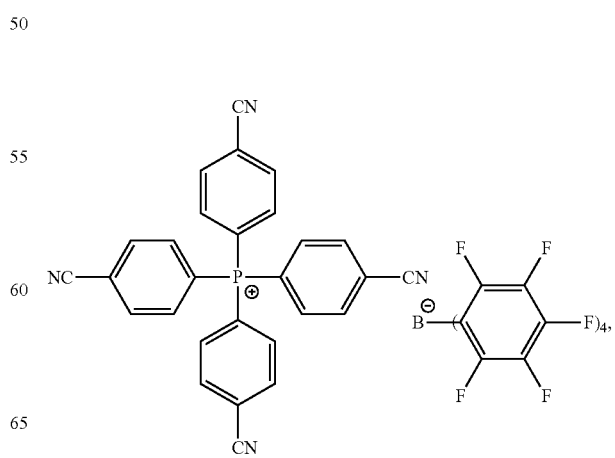

-continued

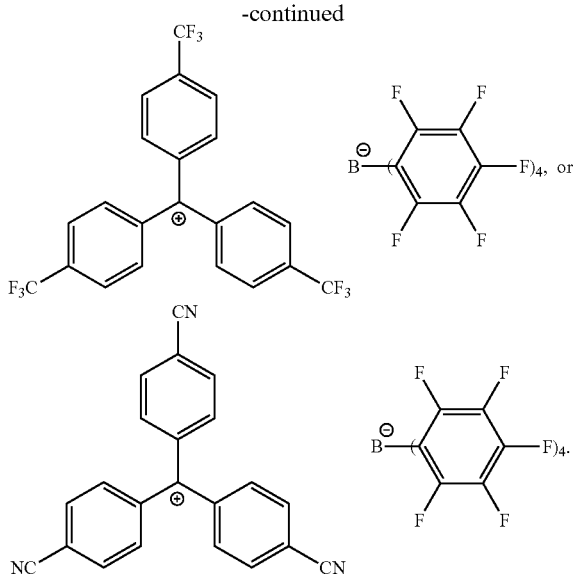

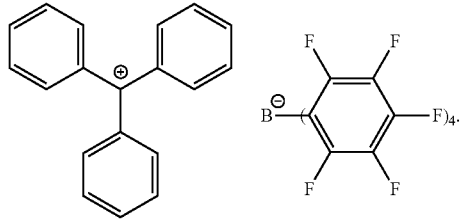

7. The polymeric charge transfer layer according to claim 6 wherein the p-dopant has the structure:

8. The polymeric charge transfer layer according to claim 3 wherein either of Monomer A, Monomer B, and Monomer C has a molecular weight of from 500 g/mole to 28000 g/mole.

9. The polymeric charge transfer layer according to claim 1 wherein either of Monomer A, and Monomer C has a purity equal to or above 99%.

10. The polymeric charge transfer layer according to claim 3 wherein either of Monomer A, Monomer B, and Monomer C has a purity equal to or above 99%.

11. An organic light emitting device comprising the polymeric charge transfer claim 1.

12. An organic electronic device comprising the polymeric charge transfer claim 1.

* * * * *